(12) United States Patent
Saukkonen et al.

(10) Patent No.: US 11,040,867 B2
(45) Date of Patent: Jun. 22, 2021

(54) SYSTEM, METHOD AND APPARATUS FOR MINIMIZING DEAD LEGS IN A BIOREACTOR SYSTEM

(71) Applicant: GLOBAL LIFE SCIENCES SOLUTIONS USA LLC, Marlborough, MA (US)

(72) Inventors: Hanna-Leena Saukkonen, Boston, MA (US); Benjamin Brown, Livingston, NJ (US); Matthew Ouellette, Newton, MA (US); Shanice Jones, Worcester, MA (US); Ralph Stankowski, Marlborough, MA (US); Eric Faldt, Akersberga (SE); Lauren Lisle, Marlborough, MA (US)

(73) Assignee: GLOBAL LIFE SCIENCES SOLUTIONS USA LLC, Marlborough, MA (US)

(*) Notice: Subject to any disclaimer, the term of this patent is extended or adjusted under 35 U.S.C. 154(b) by 30 days.

(21) Appl. No.: 16/143,827

(22) Filed: Sep. 27, 2018

(65) Prior Publication Data

US 2020/0102204 A1 Apr. 2, 2020

(51) Int. Cl.
*B67D 7/36* (2010.01)
*C12M 1/00* (2006.01)
(Continued)

(52) U.S. Cl.
CPC ............. *B67D 7/36* (2013.01); *B67D 7/0294* (2013.01); *C12M 23/14* (2013.01); *C12M 23/26* (2013.01);
(Continued)

(58) Field of Classification Search
CPC .......... B67D 7/36; B67D 7/0294; B67D 7/44; B67D 7/46; B67C 3/2625; B67C 3/2628;
(Continued)

(56) References Cited

U.S. PATENT DOCUMENTS 4,280,498 A * 7/1981 Jensen ................... A61F 5/4405
251/310
6,705,490 B1 * 3/2004 Lizerbram ............... B67D 5/60
222/145.1
(Continued)

FOREIGN PATENT DOCUMENTS

WO WO-2000004131 A1 * 1/2000
WO 2011059943 5/2011
WO 2013134515 9/2013

OTHER PUBLICATIONS

WO-2000004131-A1 English Translation of Specification (Year: 2020).*
(Continued)

*Primary Examiner* — Timothy P. Kelly
*Assistant Examiner* — Stephanie A Shrieves
(74) *Attorney, Agent, or Firm* — Grogan, Tuccillo & Vanderleeden, LLP

(57) ABSTRACT

An apparatus for minimizing dead leg spaces in a container or tubing includes a first member having a flange for attaching the first member to a wall of the container or tubing, the flange having at least one aperture, and a second member rotatably coupled to the first member, the second member having an upper end having at least one aperture, and an open distal end. The second member is rotatable relative to the first member between a closed position where the at least one aperture of the second member is misaligned with the at least one aperture in the flange to prevent the passage of fluid, and an open position where the at least one aperture of the second member is aligned with the at least one aperture in the flange to allow for the passage of fluid.

8 Claims, 27 Drawing Sheets

(51) Int. Cl.
  *B67D 7/02* (2010.01)
  *F16K 31/44* (2006.01)
  *F16K 31/50* (2006.01)

(52) U.S. Cl.
  CPC .......... *F16K 31/445* (2013.01); *F16K 31/508* (2013.01); *C12M 23/28* (2013.01)

(58) Field of Classification Search
  CPC ... B67C 3/2631; B67C 3/2617; B67C 3/2622; B67C 3/262; F16K 31/445; F16K 31/508; F16K 31/528; F16K 5/00; C12M 23/14; C12M 23/26; C12M 23/28; C12M 23/38; C12M 39/00
  USPC ...................................... 141/192; 251/84, 88
  See application file for complete search history.

(56) References Cited

U.S. PATENT DOCUMENTS

| | | | | |
|---|---|---|---|---|
| 7,134,641 | B2* | 11/2006 | Jensen | B01D 35/153 251/149.8 |
| 8,690,120 | B2* | 4/2014 | Hartnett | F16K 1/12 251/252 |
| 9,475,686 | B2* | 10/2016 | Tuohey | B67D 7/84 |
| 2005/0016620 | A1* | 1/2005 | Proulx | F16K 15/18 141/27 |
| 2011/0233210 | A1* | 9/2011 | Fatherazi | C12M 23/26 220/254.9 |
| 2012/0130329 | A1* | 5/2012 | March | F16K 3/24 604/332 |
| 2013/0167960 | A1* | 7/2013 | Pethe | B01F 15/0085 137/798 |
| 2014/0131399 | A1* | 5/2014 | Blake | F16K 3/265 251/309 |
| 2016/0090210 | A1* | 3/2016 | Vasquez | B65D 39/08 220/254.9 |
| 2017/0191016 | A1* | 7/2017 | Lee | C12M 33/00 |
| 2018/0347709 | A1* | 12/2018 | Bowdery | B01L 3/567 |

OTHER PUBLICATIONS

International Search Report issued in corresponding PCT Application No. PCT/EP2019/074358 dated Feb. 3, 2020.

* cited by examiner

SYSTEM, METHOD AND APPARATUS FOR MINIMIZING DEAD LEGS IN A BIOREACTOR SYSTEM

BACKGROUND

Technical Field

Embodiments of the invention relate generally to bioprocessing systems and methods and, more particularly, to devices for minimizing or preventing dead leg spaces in bioprocessing systems.

Discussion of Art

In the biopharmaceutical industry, increasingly, single-use or disposable containers or flexible bags are used. Such containers can be flexible or collapsible plastic bags that are supported by an outer rigid structure such as a stainless steel shell, referred to herein as a "vessel." The use of sterilized, disposable bags eliminates the time-consuming step of cleaning the steel bioreactor vessel and reduces the chance of contamination. In use, the bag is filled with the desired fluid for mixing, and an impeller disposed within the bag (driven by a magnetic drive system or motor positioned outside the vessel) is used to mix the fluid. Depending on the fluid being processed, the system may include a number of fluid lines and different sensors, probes and ports coupled with the bag for monitoring, analytics, sampling, and fluid transfer. For example, a harvest port is typically located at the bottom of the disposable bag and the vessel, and allows for a harvest line to be connected to the bag for harvesting and draining of the bag after the bioprocess is complete.

Currently available single-use bioreactors utilize hose barb or similar fittings that are welded to the bag film as entry and exit points for conveyance of fluid. The drain line fitting generally has a tubular portion that provides for one-way fluid flow. Media flows into the tubular portion of the fitting, where media, cells and other fluid components can settle and remain isolated from the bulk bioreactor environment. When cells collect in this portion of the fitting, they are generally deprived of nutrients, die, and release toxic compounds that can be detrimental to the growth and production of cells in the bulk culture. When this occurs, the area in which the media and cells collect is referred to as a dead leg or a dead leg space. For mixing systems, minimizing dead leg spaces promotes complete mixing and reduces potential sedimentation of solids.

At present, there is no effective means for preventing or completely eliminating this isolated volume of fluid and cells in a dead leg portion of a drain fitting. Existing systems typically employ a non-invasive pinch valve, whereby a clamp or other means is utilized to clamp the drain line to close the channel in the drain line tubing, however, fluid may still gather and settle in the space above the clamp.

In view of the above, there is a need for devices and methods for preventing or substantially minimizing dead leg spaces in the drain line or drain fitting of bioprocessing systems that employ single-use, flexible bioreactor containers.

BRIEF DESCRIPTION

In an embodiment, an apparatus for minimizing dead leg spaces in a container or tubing is provided. The apparatus includes a first member having a flange for attaching the first member to a wall of the container or tubing, the flange having at least one aperture, and a second member rotatably coupled to the first member, the second member having an upper end having at least one aperture, and an open distal end. The second member is rotatable relative to the first member between a closed position where the at least one aperture of the second member is misaligned with the at least one aperture in the flange to prevent the passage of fluid, and an open position where the at least one aperture of the second member is aligned with the at least one aperture in the flange to allow for the passage of fluid.

In another embodiment, an apparatus for minimizing dead leg spaces in a container or tubing includes a first member having a flange for attaching the first member to a wall of the container or tubing, and a generally hollow sleeve extending from the flange, and a plunger slidably received within the hollow sleeve, the plunger having a tip configured to sealingly engage the first member. The plunger is slidable between a closed position where the tip sealingly engages the sleeve adjacent to the flange to prevent the passage of fluid into the sleeve, and an open position where the plunger is linearly displaced from the closed position to allow for the passage of fluid into the sleeve.

In yet another embodiment, an apparatus for minimizing dead leg spaces in a container or tubing includes a first member having a flange for attaching the first member to a wall of the container or tubing, a generally hollow sleeve extending from the flange, and a sealing element extending across the sleeve for sealing off a passage through the sleeve, and a generally hollow piercing member slidably received within the hollow sleeve, the piercing member having a piercing tip. The piercing member is movable between a first position where the piercing tip is positioned below the sealing element whereby the sealing element remains intact to prevent the passage of fluid beyond the sealing element, and a second position where the piercing member pierces the sealing element and the piercing tip extends into the container or tubing and an interior of the piercing member is in fluid communication with an interior of the container or tubing to allow for passage of fluid into the hollow piercing member and beyond the sealing element.

In yet another embodiment, an apparatus for minimizing dead leg spaces in a container or tubing includes a flange for attaching the first member to a wall of the container or tubing, the flange including an opening, a main body connected to the flange, the main body having a passageway in fluid communication with the opening in the flange, a connection member connected to the main body for connecting drain tubing to the apparatus, and a valve positioned within the passageway, the valve being actuatable between a closed position in which fluid flow through the passageway is prevented, and an open position in which fluid flow through the passageway is allowed.

DRAWINGS

The present invention will be better understood from reading the following description of non-limiting embodiments, with reference to the attached drawings, wherein below:

DETAILED DESCRIPTION

Figure 1:
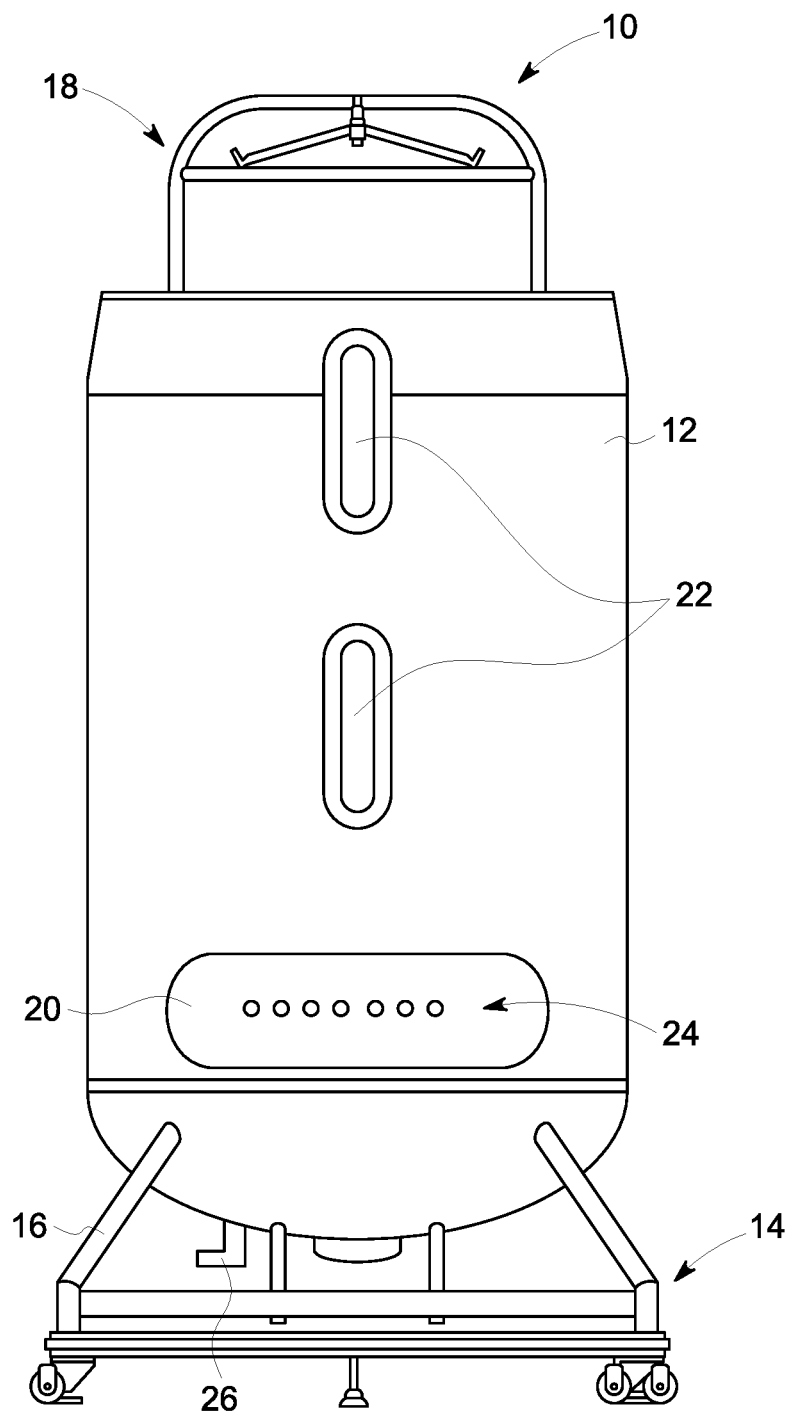
FIG. 1 is a front elevational view of a bioreactor system according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container or vessel used, for example, as a bioreactor or mixer for the contents within.

Embodiments of the invention provide various devices for minimizing dead leg in a drain port or drain line tubing of a flexible, single-use bioprocessing bag and/or achieving zero dead leg (preventing dead leg) in a drain port or drain line tubing of a flexible, single-use bioprocessing bag. As used herein, "minimizing dead leg" refers to the condition of decreasing a dead leg volume of the drain port or drain line tubing (i.e., a volume of a non-circulating length of tubing or a volume of a container in which there is no movement of liquid) as compared to the dead leg volume in the absence of the use of the apparatuses of the present invention (where a clamp may have been typically used). While embodiments of the invention are described in connection with flexible, single-use bioprocessing bags for use in the biopharmaceutical industry, it is contemplated that the devices, systems and methods for preventing or minimizing dead leg spaces described herein can likewise be used in containers, containers, tubing and vessels, more generally. As used here, the terms "upper member" and "first member" are used interchangeably to refer to the same components, as are the terms "lower member" and "second member".

With reference to FIG. 1, a bioreactor system 10 according to an embodiment of the invention is illustrated. The bioreactor system 10 includes a generally rigid bioreactor vessel or support structure 12 mounted atop a base 14 having a plurality of legs 16. The vessel 12 may be formed, for example, from stainless steel, polymers, composites, glass, or other metals, and may be cylindrical in shape, although other shapes may also be utilized without departing from the broader aspects of the invention. The vessel 12 may be outfitted with a lift assembly 18 that provides support to a single-use, flexible bag 20 disposed within the vessel 12. The vessel 12 may include one or more sight windows 22, which allows one to view a fluid level within the flexible bag 20, as well as a window 24 positioned at a lower area of the vessel 12. The window 24 allows access to the interior of the vessel 12 for insertion and positioning of various sensors and probes (not shown) within the flexible bag 20, and for connecting one or more fluid lines to the flexible bag 20 for fluids, gases, and the like, to be added or withdrawn from the flexible bag 20. Sensors/probes and controls for monitoring and controlling important process parameters include any one or more, and combinations of: temperature, pressure, pH, dissolved oxygen (DO), dissolved carbon dioxide ($pCO_2$), mixing rate, and gas flow rate, for example. The vessel 12 may also include an opening in the bottom thereof, allowing for drain or discharge tubing 26 to connect with the flexible bag 20 via welding or other connectors for draining and/or harvesting the contents of the flexible bag 20.

In embodiments of the invention, the drain outlet of the flexible bag 20 may be configured or outfitted with a device configured to minimize or prevent dead leg spaces in the drain tubing 26, associated connectors and/or adjacent areas of the flexible bag 20. FIGS. 2-6 illustrate one possible configuration of an apparatus 100 that can be integrated with the flexible bag 20 to prevent dead leg spaces in the flexible bag 20 and discharge tubing 26. As shown therein, the apparatus 100 includes a first, upper member 110 and a second, lower member 112 that is configured for rotatable coupling to the upper member 110. With specific reference to FIGS. 2 and 3, the upper member 110 includes an annular flange 114 and a hollow stem 116 that extends downwardly from the flange 114. The flange 114 includes a plurality of apertures 118 formed therein that are each spaced a radial distance from a central axis 120 of the upper member 110 and provide a passageway for a fluid to pass through the flange 114 and into the interior portion of the hollow stem 116 as discussed below. The distal end of the stem 116 also includes at least one projection or pin 121 extending outwardly therefrom, the purpose of which will be described hereinafter.

Figure 4:
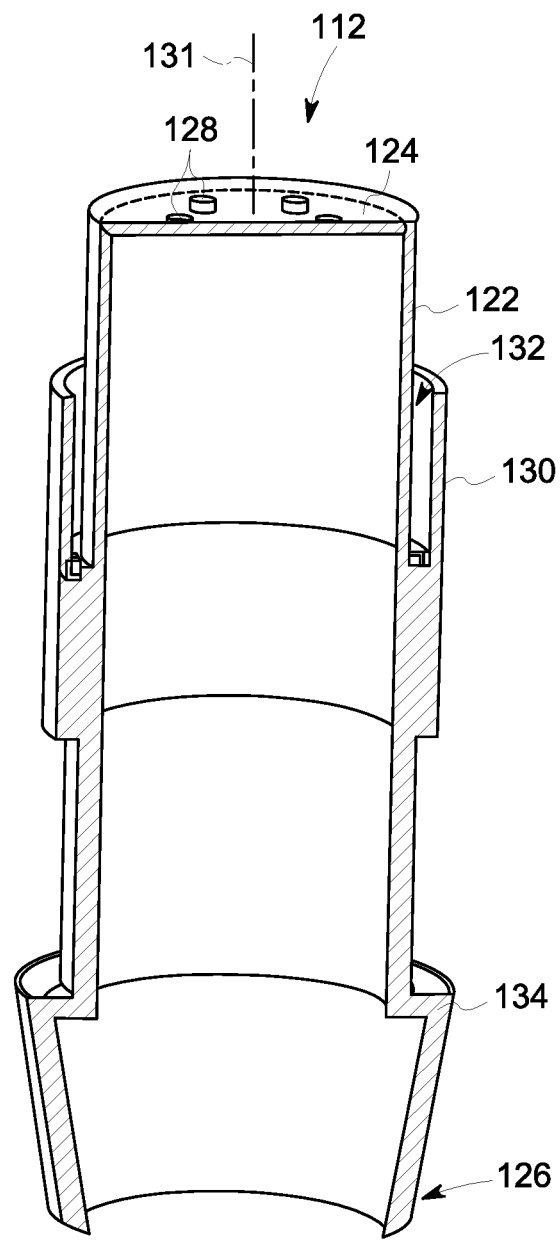
FIG. 4 is a perspective, cross-sectional view of a lower member of the apparatus of FIG. 2.
Figure 5:
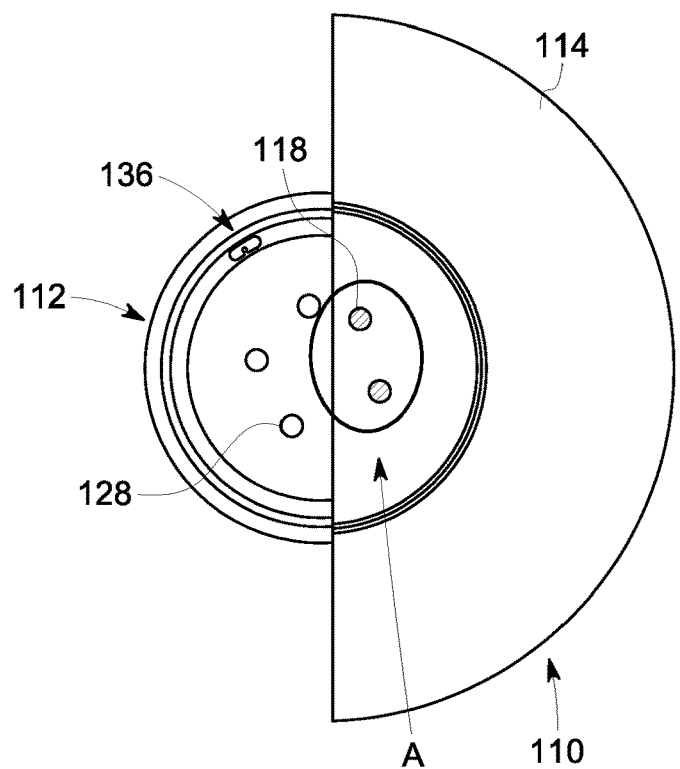
FIG. 5 is a partial cutaway, top plan view of the apparatus of FIG. 2, illustrating a closed position whereby fluid flow is prevented.
Figure 6:
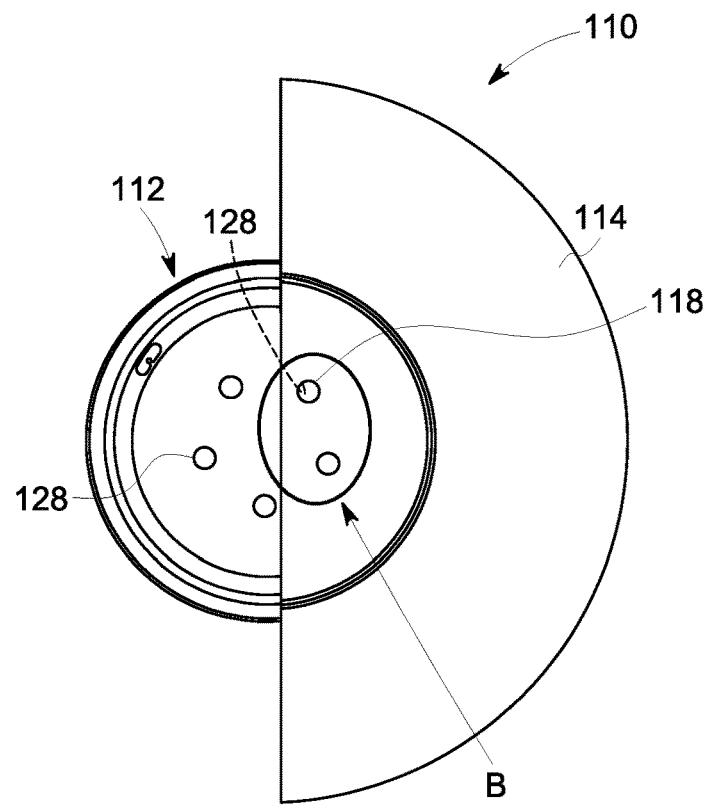
FIG. 6 is a partial cutaway, top plan view of the apparatus of FIG. 2, illustrating an opening position whereby fluid flow is enabled.

As shown in FIG. 4, the lower member 112 includes a generally tubular body portion 122 having a generally closed upper end 124 and an open bottom end 126. The upper end includes a plurality of apertures 128 formed therein that are each spaced a radial distance from a central axis 131 of the lower member 112 that corresponds to the distance that the apertures 118 of the upper member 110 are spaced from central axis 120. In addition, the angular spacing of apertures 128 of the lower member 112 corresponds to the angular spacing of the apertures 118 of the upper member 110. As further shown in FIG. 4, the body portion 122 includes an outwardly spaced annular sleeve or sidewalls 130 defining an annular slot 132 for receiving the stem 116 of the upper member 110. In this respect, the inner diameter of the sleeve 130 generally corresponds to the outer diameter of stem 116, and the inner diameter of the stem 116 generally corresponds to the outer diameter of the body portion 122. As alluded to above, and as shown in FIGS. 5 and 6, the lower member 112 also includes a keyway 136 configured to receive the projection 121 of the upper member 110 for selectively locking the apparatus in an open and/or closed position. In an embodiment, the distal end 126 of the lower member 112 may include a hose barb connection 134 (or TC connection) for connection to drain tubing 26, as shown in FIG. 2.

Figure 2:
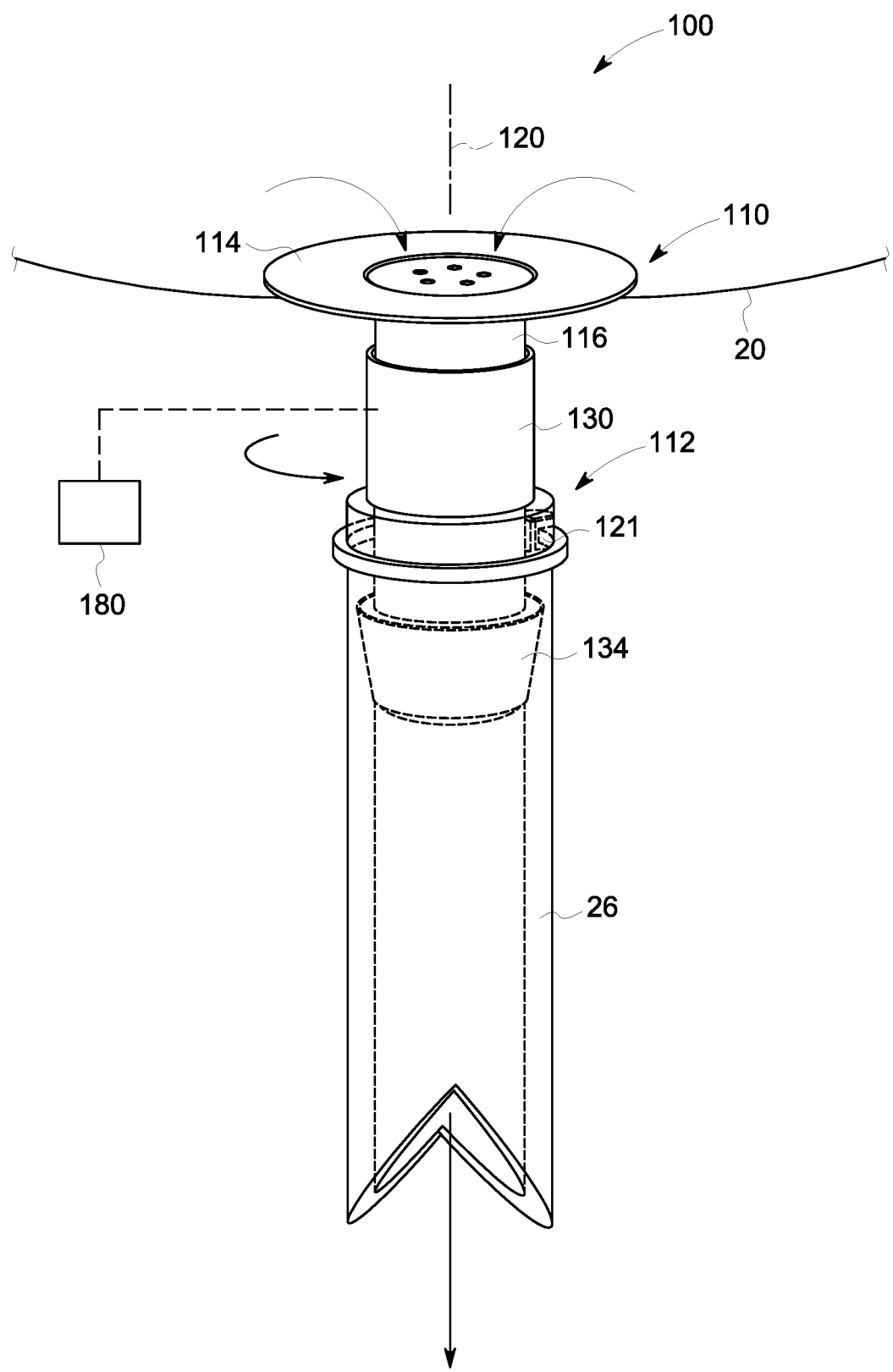
FIG. 2 is a perspective view of an apparatus for minimizing dead leg spaces in a bioprocessing system, according to an embodiment of the invention.
Figure 3:
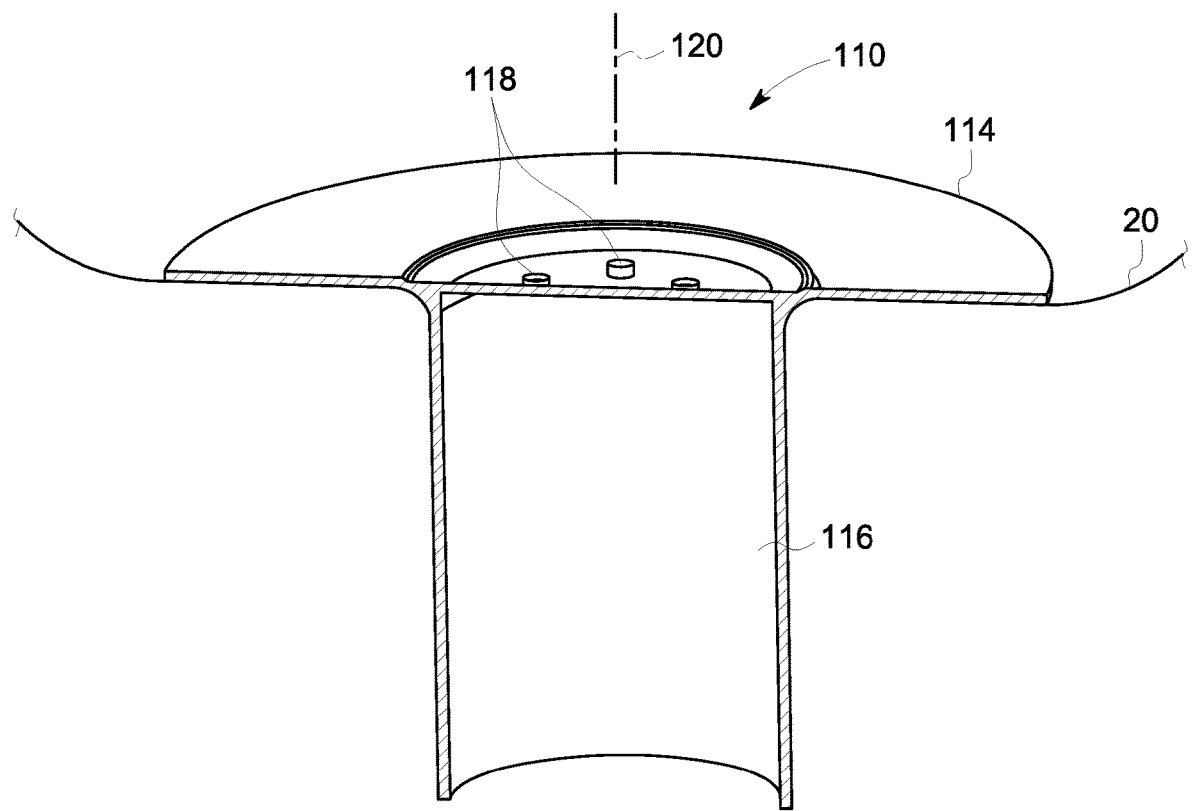
FIG. 3 is a perspective, cross-sectional view of an upper member of the apparatus of FIG. 2.

Referring still further to FIG. 2, the flange 114 is sealingly attached to the inner surface of the flexible bag 20, such as by welding, although other means of attachment may also be utilized without departing from the broader aspects of the invention. The stem 116 of the upper member 110 is slidably and rotatably received within the annular slot 132 in the lower member 112. In use, flexible bag 20 with integrated apparatus 100 is positioned within a bioreactor vessel 12 such that apparatus 100 extends through the drain opening/aperture in the bottom of the vessel 12 and is connected to drain tubing/line 26, as illustrated in FIGS. 1 and 2.

With reference to FIGS. 5 and 6, the lower member 112 is rotatable relative to the upper member 110 to selectively align (or misalign) the apertures 118, 128. In particular, prior to filling the flexible bag 20 with process media and prior to commencing bioprocessing, the lower member 112 is rotated to a closed position so that apertures 128 in the lower member 112 are not aligned with the apertures 118 in the upper member 100, as shown in area A of FIG. 5. This orientation prevents fluid flow through the apparatus 100 and out of the flexible bag 20. Because the flange 114 of the upper member 110 is substantially planar with the bottom of the flexible bag 20, dead leg spaces at a location lower than the bottom of the flexible bag 20, such as in discharge tubing 26, are prevented or substantially minimized. After processing, or at any time desired, the lower member 112 may be rotated relative to the upper member 110 to bring the apertures 118 in the upper member 110 into alignment with the apertures 128 in the lower member, as shown in area B of FIG. 6, which allows fluid to flow from the flexible bag 20, through the apparatus 100, and into the connected discharge/drain tubing 26. In an embodiment, the projection 121 and keyway 136 are operable to lock the apparatus 100 in this open position.

The apparatus 100 is therefore selectively operable to prevent or allow fluid flow from the flexible bag 20 and into the drain tubing 20. In the closed position, where the apertures are misaligned, because flange 114 and apertures 118, 128 are substantially flush with the bottom of the flexible bag 20, no fluid is permitted to pass by the flange 114 and collect outside the primary volume of the flexible bag 20 (i.e., outside of the regulated bioreactor environment), such as in the drain tubing 26. In an embodiment, it is contemplated that the lower member 112 may be connected to a motor or other rotational drive mechanism 180, allowing for automated control over the position of the apparatus 100.

Figure 7:
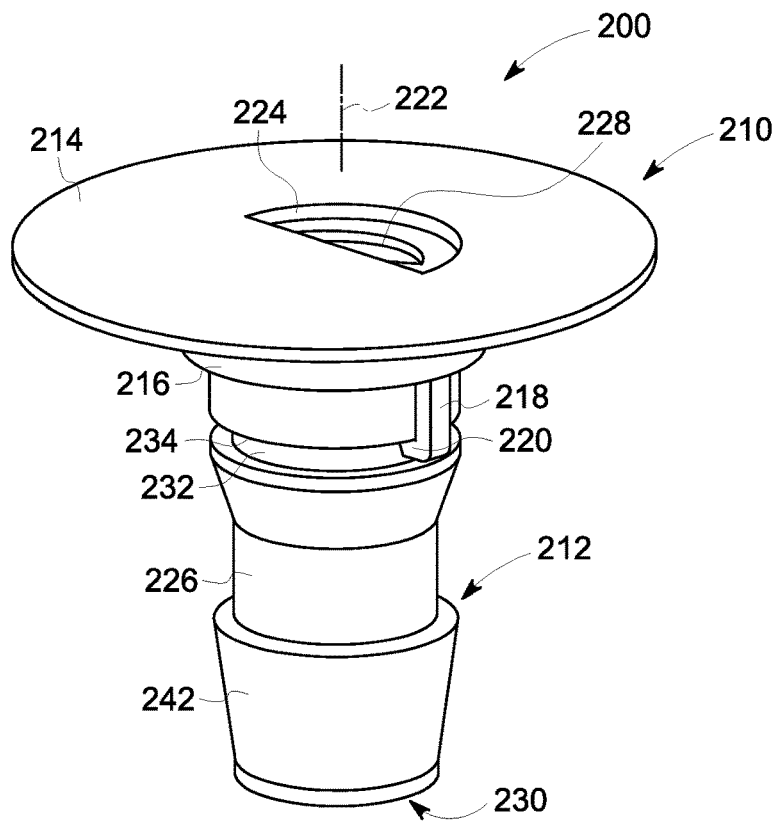
FIG. 7 is a perspective view of another apparatus for minimizing dead leg spaces in a bioprocessing system, according to another embodiment of the invention, showing an open position whereby fluid flow is enabled.

FIGS. 7-10 illustrate another configuration of an apparatus 200 that can be integrated with the flexible bag 20 to prevent or minimize dead leg spaces in the flexible bag 20 and discharge tubing 26. As illustrated therein, the apparatus 200 is generally similar in configuration and operation to the apparatus 100 of FIGS. 2-6, and includes an upper member 210 and a lower member 212 that is rotatably coupled to the upper member 210. The upper member 210 has an annular flange 214, a short, hollow stem 216 that extends downwardly from the flange 214, and a pair of resilient arms 218 extending downwardly from the stem 216. In an embodiment, the resilient arms 218 are spaced approximately 180 degrees apart and include projections 220 and their respective distal ends that extend towards a center line or central axis 222 of the apparatus 200. As illustrated in FIG. 7, the flange 214 includes at least one aperture 224 formed therein, which provides a passageway for a fluid to pass through the flange 214 and into the interior portion of the hollow stem 216, as discussed below. In an embodiment, the aperture 224 is a half-circle in shape, although other shapes may be utilized without departing from the broader aspects of the invention.

Figure 9:
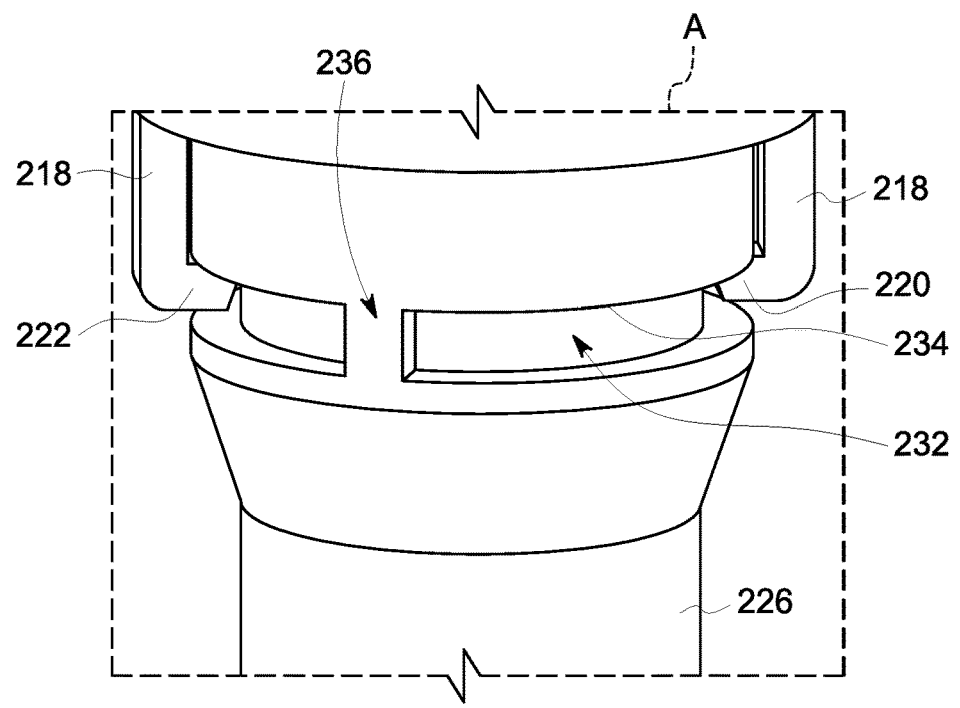
FIG. 9 is an enlarged, detail view of area A of FIG. 8.
Figure 10:
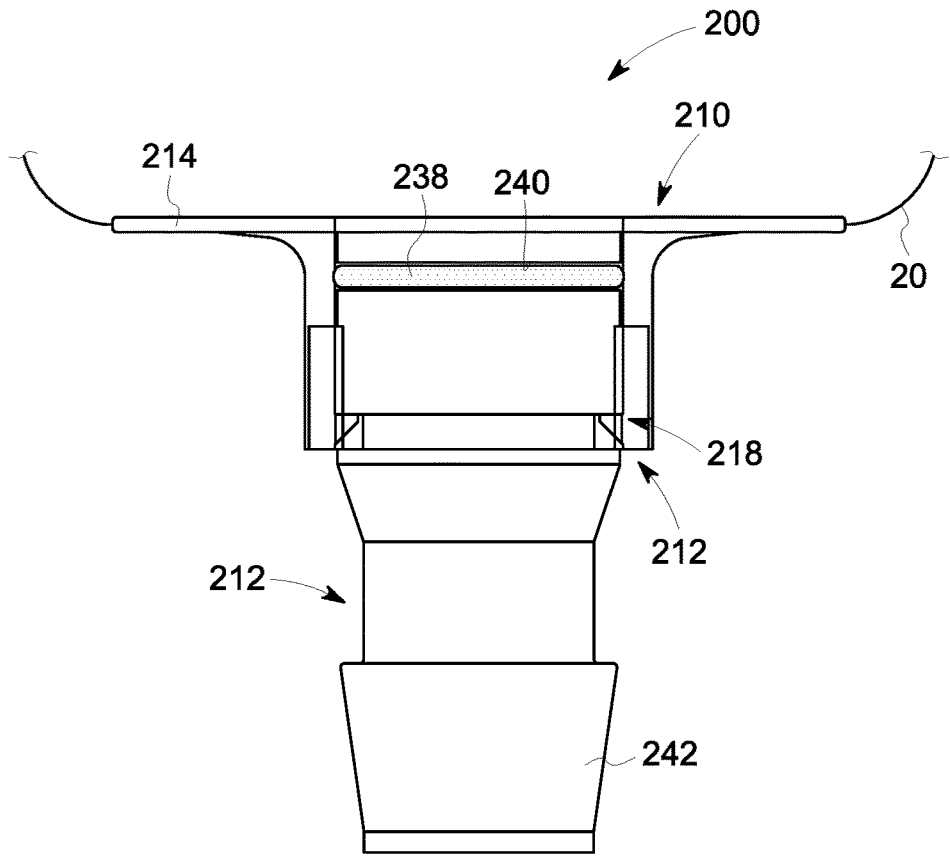
FIG. 10 is a side, cross-sectional view of the apparatus of FIG. 7.

With further reference to FIG. 7, the lower member 212 includes a generally hollow, tubular body portion 226 having an upper end 227 with an aperture 228 formed therein and a generally open bottom end 230. In an embodiment, the aperture 228 is, like aperture 224, half-circle in shape, although other shapes are possible. As shown in FIGS. 7 and 9, the body portion 226 of the lower member 212 also includes a circumferential groove 232 that defines a shoulder 234. The circumferential groove 232 is interrupted by at least one position stop 236, the purpose of which will be described hereinafter. With reference to FIG. 10, the upper portion of the lower member 212 may also include a sealing element 238 disposed in a circumferential groove 240. In an embodiment, the distal end 230 of the lower member 212 may include a hose barb connection 242 for connection to drain tubing (not shown).

As best shown in FIG. 10, the flange 214 of the upper member 210 is sealingly attached to the inner surface of the flexible bag 20, such as by welding, although other means of attachment may also be utilized without departing from the broader aspects of the invention. The lower member 212 is received within the hollow stem 216 of the upper member 210 such that the O-ring 238 sealingly engages the interior surface of the stem 216 to prevent the passage of fluid therebetween. When the lower member 212 is fully received within the stem 216, the resilient arms 218 of the upper member 210 are received within the circumferential groove 232 of the body portion 226 of the lower member 212. In this position, the projections 220 on the ends of the resilient arms 218 contact the shoulder 234, preventing decoupling of the upper member 210 and lower member 212 from one another. In an embodiment, the apparatus 200 may also include a D-shaped O-ring (not shown) (or other shape configured to correspond to the shape of the apertures 224, 228) positioned between the apertures 224, 228 to allow for fluid sealing between the rotating elements that prevents fluid leakage when in the closed position, as discussed below.

Figure 8:
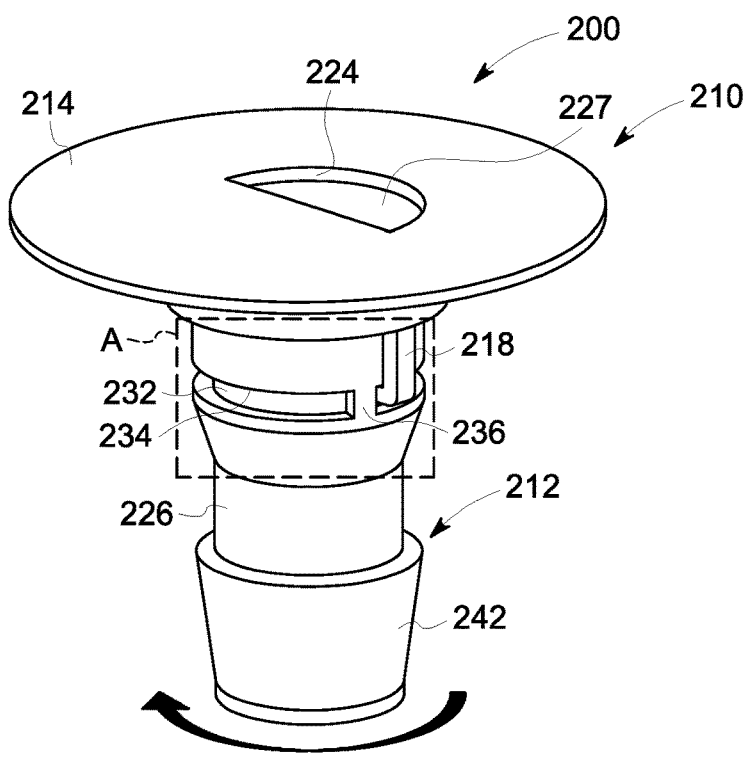
FIG. 8 is a perspective view of the apparatus of FIG. 7, showing a closed position whereby fluid flow is prevented.

In use, flexible bag 20 with integrated apparatus 200 is positioned within a bioreactor vessel 12 such that apparatus 200 extends through the drain opening/aperture in the bottom of the vessel 12 and is connected to drain tubing/line 26. Referring once again to FIGS. 7 and 8, the lower member 212 is rotatable relative to the upper member 210 to selectively align (or misalign) the apertures 224, 228. In particular, prior to filling the flexible bag 20 with process media and prior to commencing bioprocessing, the lower member 212 is rotated to a closed position so that the aperture 228 of the lower member is out of alignment with the aperture 224 in the flange 214, as shown in FIG. 8. In this position, the closed upper surface 227 of the lower member 212 is presented below the aperture 224. This orientation prevents fluid flow through the apparatus 200 and out of the flexible bag 20. Because the flange 214 of the upper member 210 is substantially flush with the bottom of the flexible bag 20, dead leg spaces at a location lower than the bottom of the flexible bag 20, such as in discharge tubing 26, are prevented or substantially minimized. After processing, or at any time desired, the lower member 212 may be rotated relative to the upper member 210 in the direction of arrow B to bring the apertures 224, 228 into vertical alignment with one another, which allows fluid to flow from the flexible bag 20, through the apparatus 200, and into the connected discharge/drain tubing 26. The position stops 236 functions to prevent over-rotation of the lower member 212, and are positioned so that when the lower member 212 is rotated in one direction until the projections 220 contact the position stop 236, the apparatus 200 is in the closed position, and when the lower member 212 is rotated in an opposite direction until the projections 220 contact an opposed position stop 236, the apparatus 200 is in the open position where the apertures 224, 228 are aligned. In this respect, the position stops 236 provide a tactile indication of a fully open and fully closed position of the apparatus 200.

The apparatus 200 is therefore selectively operable to prevent or allow fluid flow from the flexible bag 20 and into the drain tubing 20. In the closed position, where the apertures are misaligned, because flange 214 and apertures 224, 228 are substantially flush with the bottom of the flexible bag 20, no fluid is permitted to pass by the flange 214 and collect outside the primary volume of the flexible bag 20, such as in the drain tubing 26. As discussed above, in an embodiment, it is contemplated that the lower member 212 may be connected to a motor or other rotational drive mechanism, allowing for automated control over the position of the apparatus 200. Moreover, in an embodiment, the apparatus 200 may include a locking mechanism for selectively locking the apparatus 200 in the open or closed position, as desired.

Figure 11:
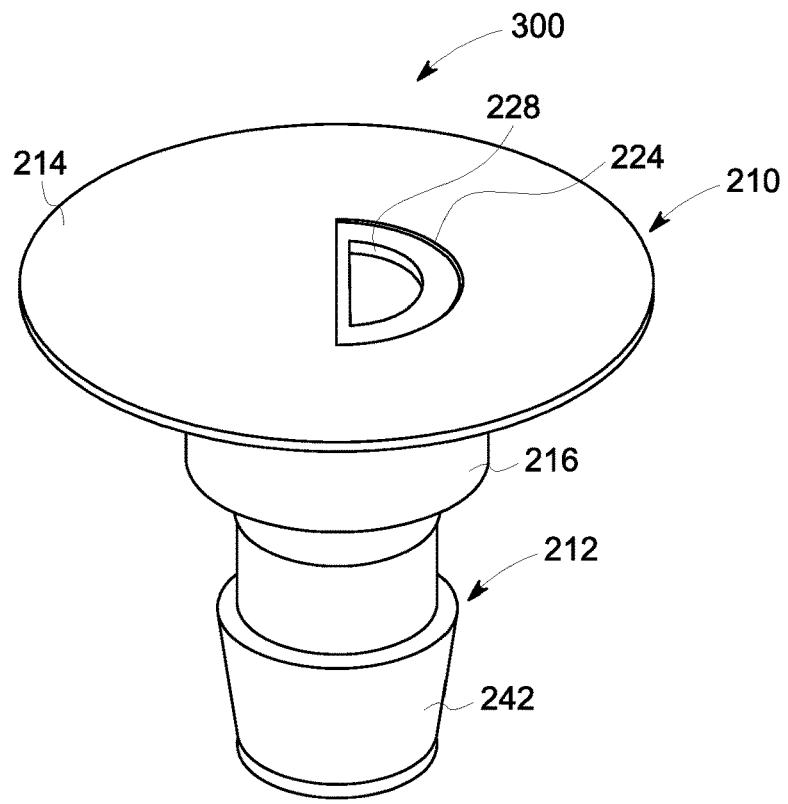
FIG. 11 is a perspective view of another apparatus for minimizing dead leg spaces in a bioprocessing system, according to another embodiment of the invention.
Figure 12:
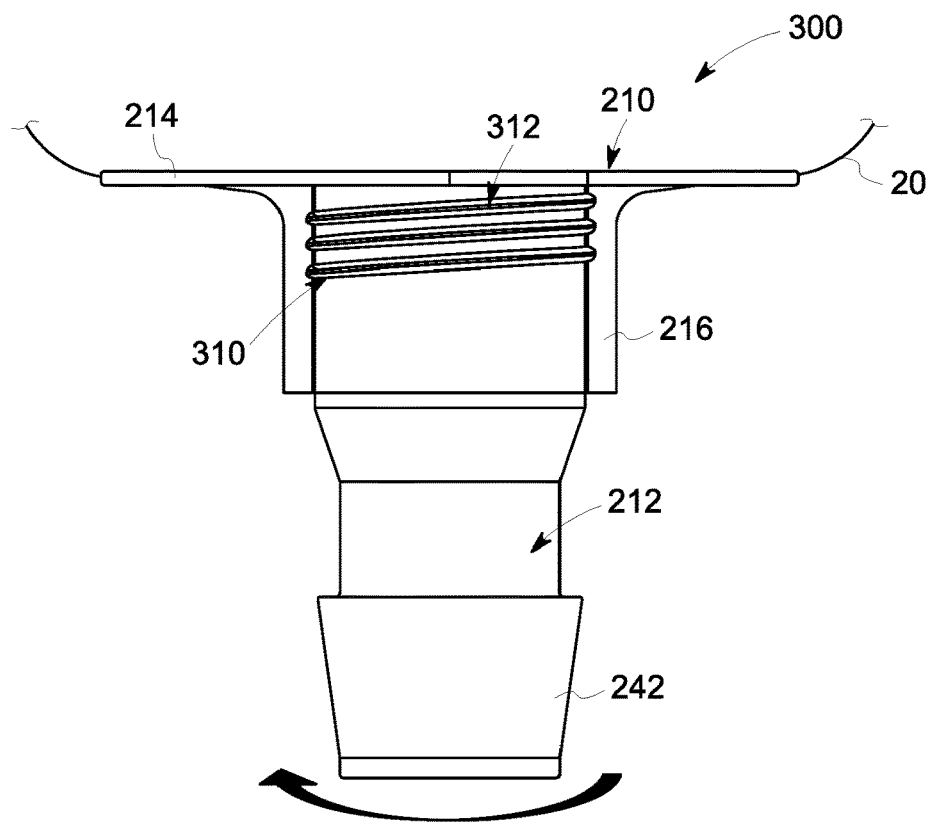
FIG. 12 is a side, cross-sectional view of the apparatus of FIG. 11.

FIGS. 11 and 12 depict another apparatus 300 that can be integrated with the flexible bag 20 to prevent or minimize dead leg spaces in the flexible bag 20 and discharge tubing 26. The apparatus 300 is substantially similar in configuration and operation to the apparatus 200 of FIGS. 7-10, where like reference numerals indicate like parts. As illustrated in FIG. 12, however, rather than utilizing resilient arms that are received in a circumferential slot to guide rotation of the lower member with respect to the upper member, apparatus 300 employs a tapered threaded portion 310 (having one of male or female threads) on an external surface of an upper portion of the lower member 212 that is configured to be threadedly received by a corresponding tapered threaded portion 312 (having the other of male or female threads) on an inner surface of the stem 216 of the upper member 210. In this respect, the upper and lower members 210, 212 of the apparatus 300 are threadedly and rotatably coupled to one another. In use, a user can rotate the lower member 212 to selectively align (or misalign) the aperture 228 of the lower member 212 with the aperture 224 of the upper member 210 to facilitate or prevent draining of the bag 20, as desired. In an embodiment, the apparatus 300 may also include a D-shaped o-ring (not shown) (or other shape configured to correspond to the shape of the apertures 224, 228) positioned between the apertures 224, 228 to allow for fluid sealing between the rotating elements that prevents fluid leakage when in the closed position, as discussed below.

Like apparatuses 100 and 200, it is similarly contemplated that the lower member 212 may be connected to a motor or other rotational drive mechanism, allowing for automated control over the position of the apparatus 300.

Figure 13:
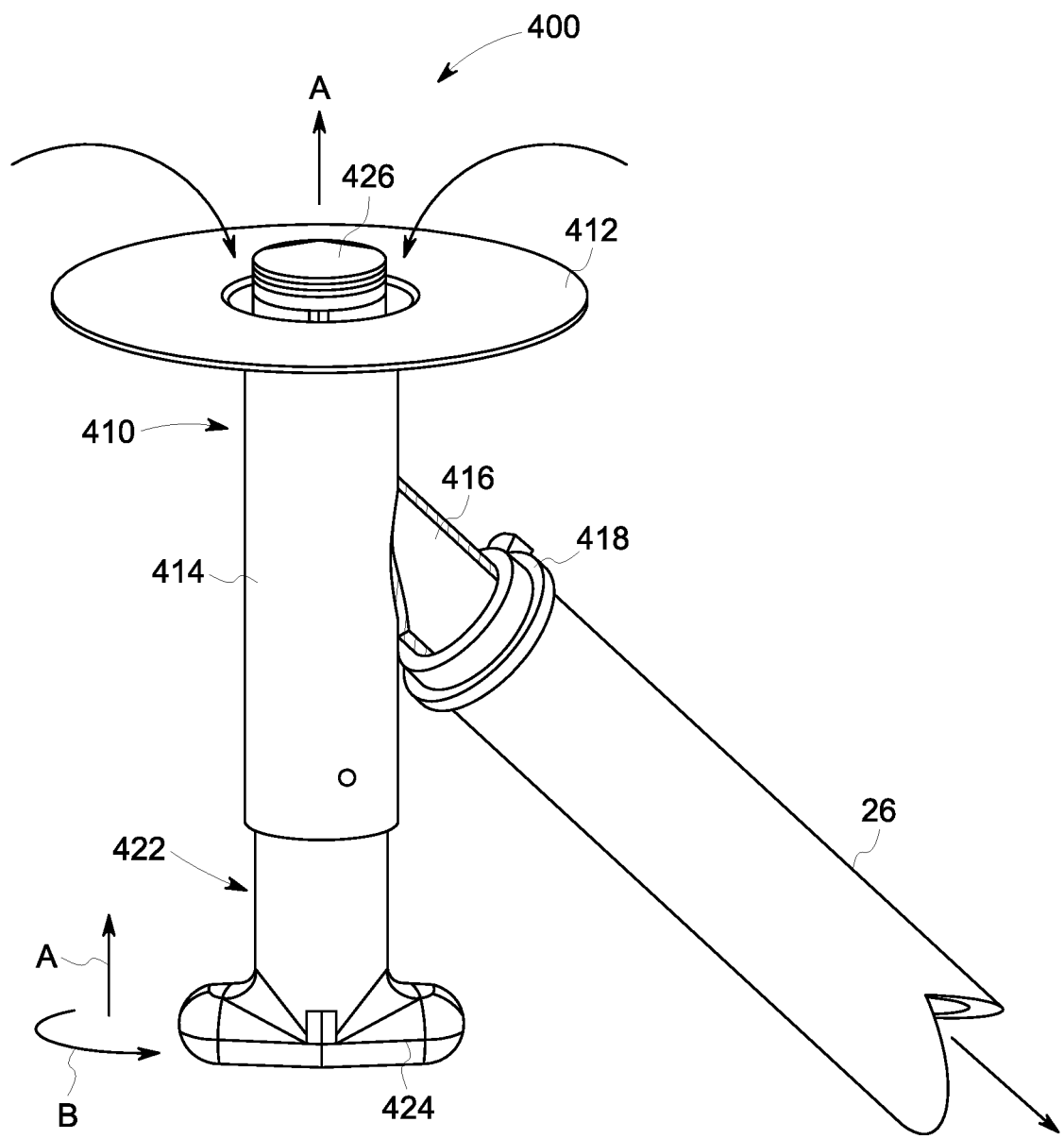
FIG. 13 is a perspective view of another apparatus for minimizing dead leg spaces in a bioprocessing system, according to another embodiment of the invention.
Figure 14:
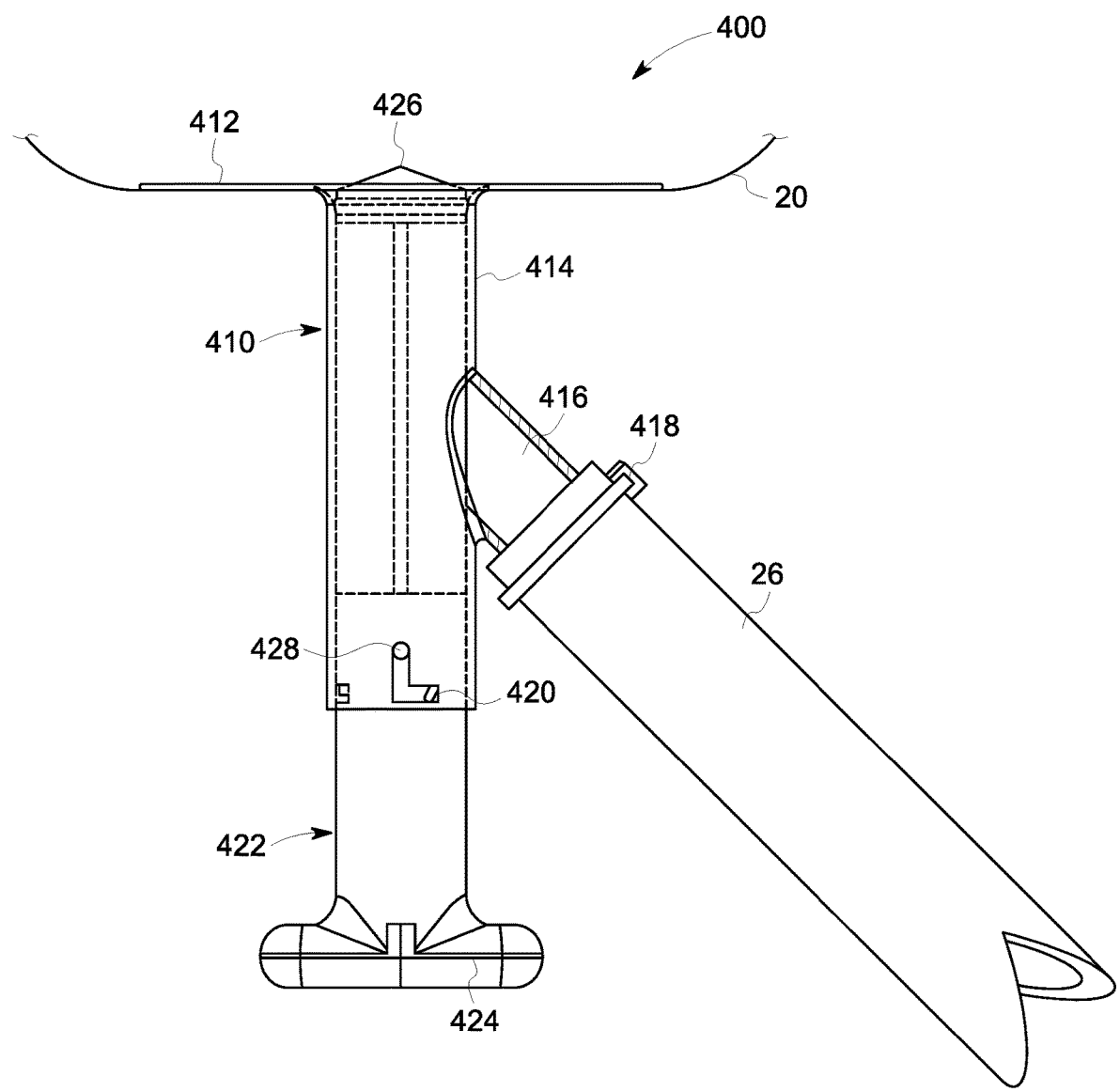
FIG. 14 is a perspective view of the apparatus of FIG. 13, showing a closed position whereby fluid flow is prevented.
Figure 15:
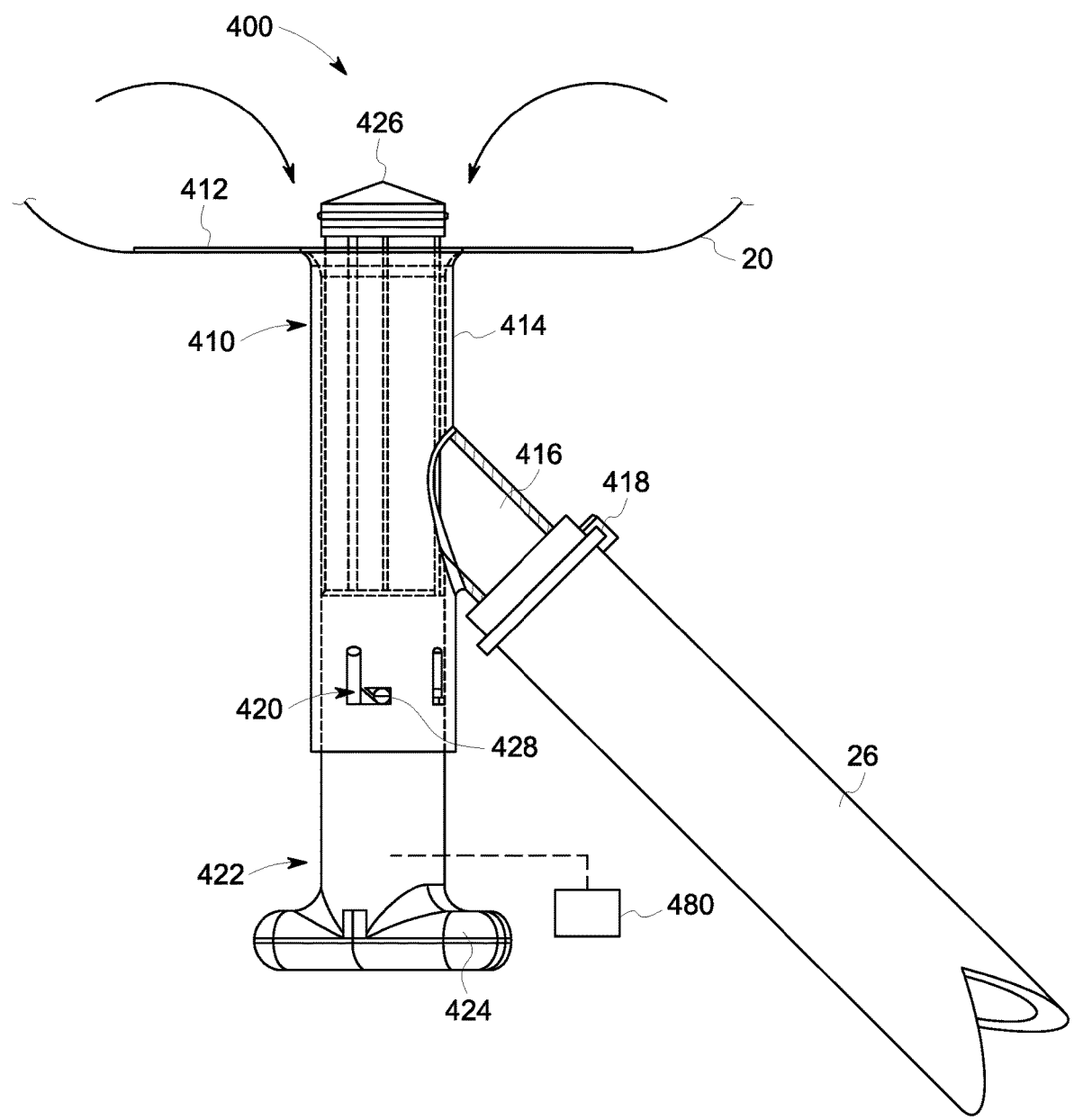
FIG. 15 is a perspective view of the apparatus of FIG. 13, showing an open position whereby fluid flow is enabled.

Turning now to FIGS. 13-15, yet another apparatus 400 for preventing dead leg spaces in a bioprocessing system is illustrated. The apparatus 400 includes an upper member 410 having a generally annular flange 412 and a hollow tube or sleeve 414 that extends downwardly and substantially perpendicularly from the flange 412. The upper member 410 further includes a Y-leg or branch tube 416 that extends downwardly at an angle from the sleeve 414. In an embodiment, the branch tube 416 may be a T-leg. As illustrated in FIG. 13, a drain line or tubing 26 may be connected to the end of the branch tube 416 using a clamp 418, although other means of connection such as a hose barb on the distal end of the branch tube 416 may also be utilized without departing from the broader aspects of the invention. In an embodiment, the sleeve 414 may be configured with a radial projection or lug 428, the purposed of which will be discussed hereinafter.

With further reference to FIGS. 13-15, the apparatus 400 further includes a plunger 422 that is slidably received by the sleeve 414 through an open bottom end thereof. The plunger 422 has a lower end that terminates in a T-shaped handle 424 providing for ergonomic gripping, and an upper end having a plunger tip 426 having an integrated sealing element that sealingly engages an inner wall of the sleeve 414. The body of the plunger is configured with relieved portions, fluted portions, or a smaller diameter than the tip 426 to allow for fluid flow past the tip, as discussed hereinafter. As best shown in FIGS. 14 and 15, the plunger 422 also includes a keyway 420 that is configured to receive lug 428 on the sleeve 414. As illustrated in FIGS. 14 and 15, the keyway 420 may be generally L-shaped.

In use, the flange 412 is attached to the inner surface of the flexible bag 20, such as by welding, although other means of attachment may also be utilized without departing from the broader aspects of the invention. The drain tubing 26 is then secured to the branch leg 416 and the plunger 422 is received in the sleeve 414 such that the lug 428 is positioned in the keyway 420. As shown in FIG. 14, in a closed position, the plunger tip is seated within the sleeve 414 and generally below the flange 412, preventing any fluid flow past the flange 412 and out of the flexible bag 20. In this position, the lug 428 is received in the upper-most part of the keyway 420. With reference to FIGS. 13 and 15, when draining of the bag 20 is desired, the plunger 422 is urged upward in the direction of arrow A, causing the plunger to protrude above the flange 412, allowing fluid to flow past the tip 426, into the sleeve 414, through the branch leg 416 and into the drain tubing 26. Once the plunger is pushed upwardly to the open position, it can also be rotated in the direction of arrow B, to position the lug 428 within the lower portion/leg of the keyway 420, as shown in FIG. 15. This essentially locks the plunger 422 in the open position, preventing it from moving upwardly or downwardly with respect to the sleeve 414.

While FIGS. 13-15 illustrate an embodiment whereby the plunger is urged upwardly to break the seal between the plunger tip 426 and the interior of the sleeve 414 to allow fluid to drain from the bag 20, in other embodiments, the apparatus 400 may be configured so that the plunger can be retracted below the branch leg 416 to allow the contents of the bag 20 to drain into the branch leg 416 and connected drain tubing 26. Moreover, as alluded to above, in an embodiment, the plunger may be connected to an actuator 480 or motor allowing for automated operation of the apparatus 400. As discussed above in connection with the previous embodiments, the apparatus 400 eliminates any cavity below the bottom of the flexible bag 20 within which fluid can accumulate. In this respect, the apparatus 400 of the invention prevents dead leg spaces which can adversely affect the batch being processed.

Figure 16:
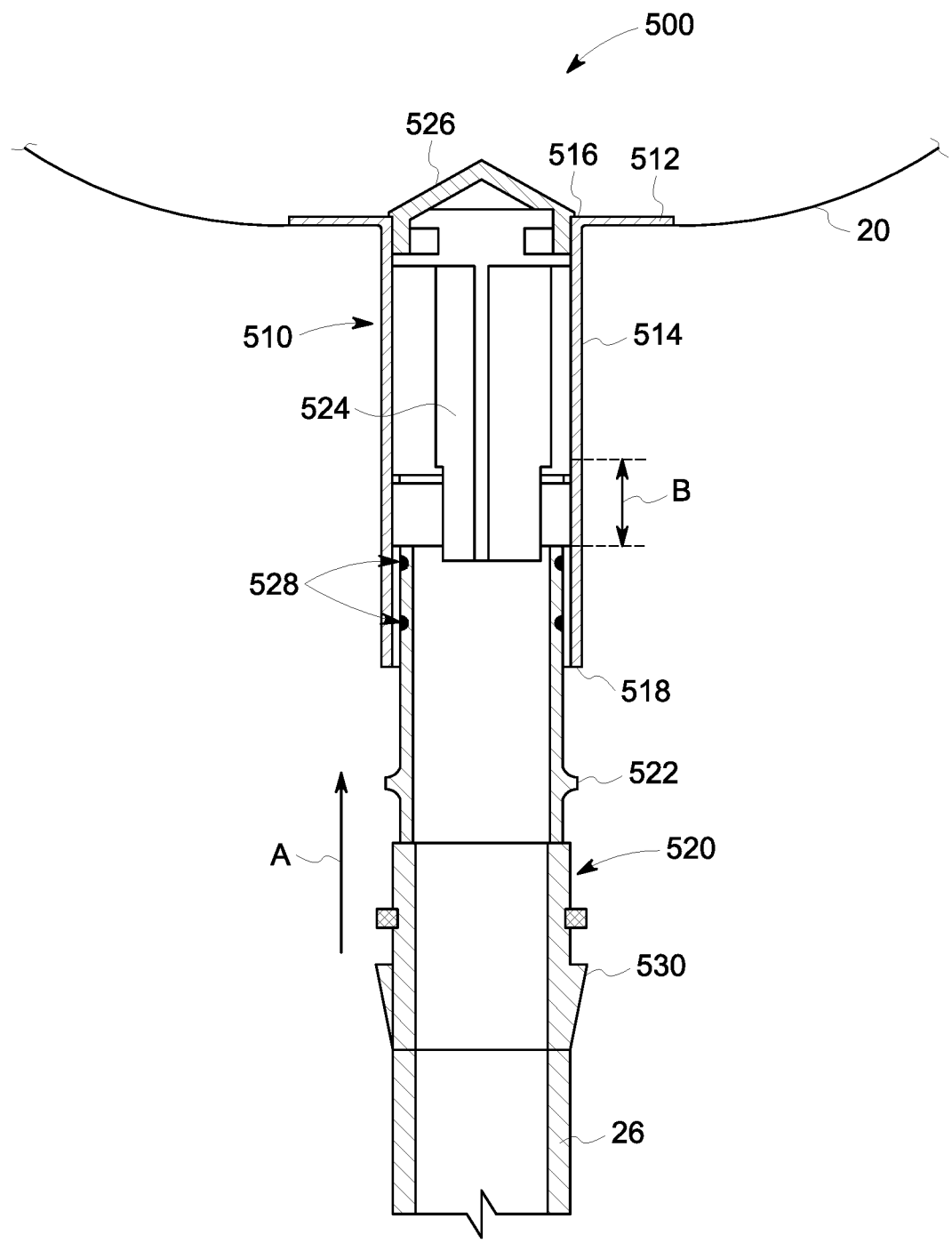
FIG. 16 is a side, cross-sectional view of an apparatus for minimizing dead leg spaces in a bioprocessing system according to another embodiment of the invention, showing a closed position whereby fluid flow is prevented.
Figure 17:
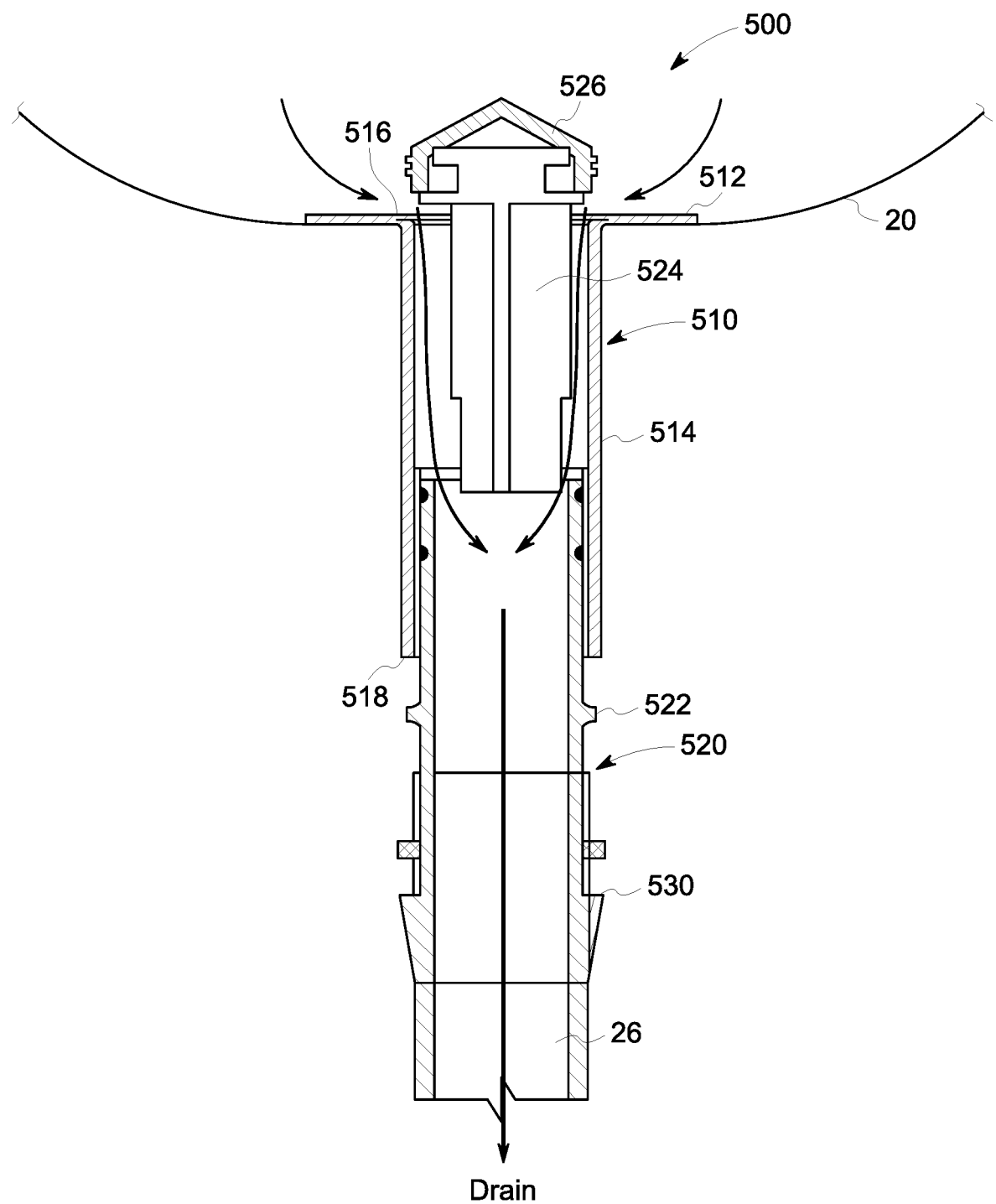
FIG. 17 is a side, cross-sectional view of the apparatus of FIG. 16, showing an open position whereby fluid flow is enabled.

FIGS. 16 and 17 illustrate an apparatus 500 according to another embodiment of the invention that can be integrated with the flexible bag 20 to prevent or minimize dead leg spaces in the flexible bag 20 and discharge tubing 26. The apparatus 500 is substantially similar in configuration and operation to the apparatus 400 of FIGS. 13-15. In particular, the apparatus 500 includes an upper member 510 having a flange 512 configured for attachment to flexible bag 20 in the manner described above, and a generally cylindrical and hollow sleeve 514 that extends downwardly from the flange 512, the sleeve having an open top end 516 and an open bottom end 518. The apparatus 500 also includes a plunger 520 that is slidably received within the sleeve hollow tube or sleeve 514 through the open bottom end 518. The plunger 520 has a generally hollow cylindrical first portion 522, a fluted, second portion 524 extending from the first portion 522, and a conical tip 526 connected to the second portion 524. The tip 526 is dimensioned so as to form a fluid-tight seal with the interior sidewalls of the sleeve 514 when the tip is received by the sleeve 514, as illustrated in FIG. 16. In an embodiment, the tip 526 may be covered or formed with silicone. As also shown in FIG. 16, the cylindrical portion 522 of the plunger 520 includes one or more sealing elements 528, such as O-rings, that likewise form a fluid-tight seal with the sleeve 514. A distal end of the plunger 520 may be formed with a hose-barb connection 530 for connecting drain tubing 26.

With further reference to FIG. 16, in a closed position, the tip 526 is retracted within the sleeve 514 and forms a seal with the sleeve 514 to prevent the passage of fluid out of the bag 20. With reference to FIG. 17, when draining of the bag 20 is desired, the plunger may be urged upward, in the direction of arrow A, along a path of travel, B, causing the tip 526 to unseat from the sleeve 514. In this position, fluid is permitted to flow past the tip, through the fluted portion 524 of the plunger, through the hollow cylindrical portion 522 and into the attached drain tubing 26. In this manner, the apparatus 500 operates substantially similarly to the apparatus 400 of FIGS. 13-15.

Figure 18:
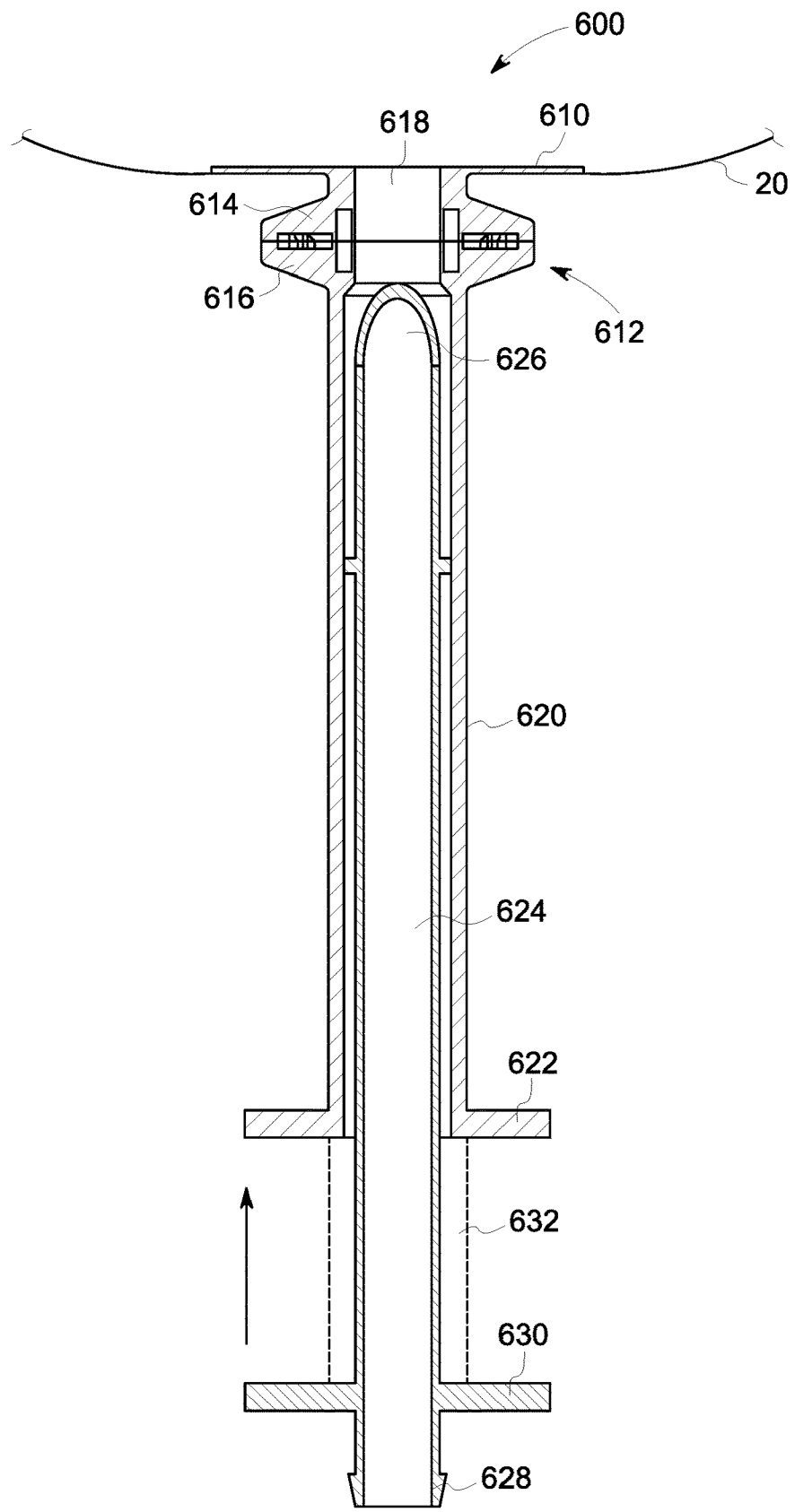
FIG. 18 is a side, cross-sectional view of an apparatus for minimizing dead leg spaces in a bioprocessing system according to another embodiment of the invention, showing a closed position whereby fluid flow is prevented.
Figure 19:
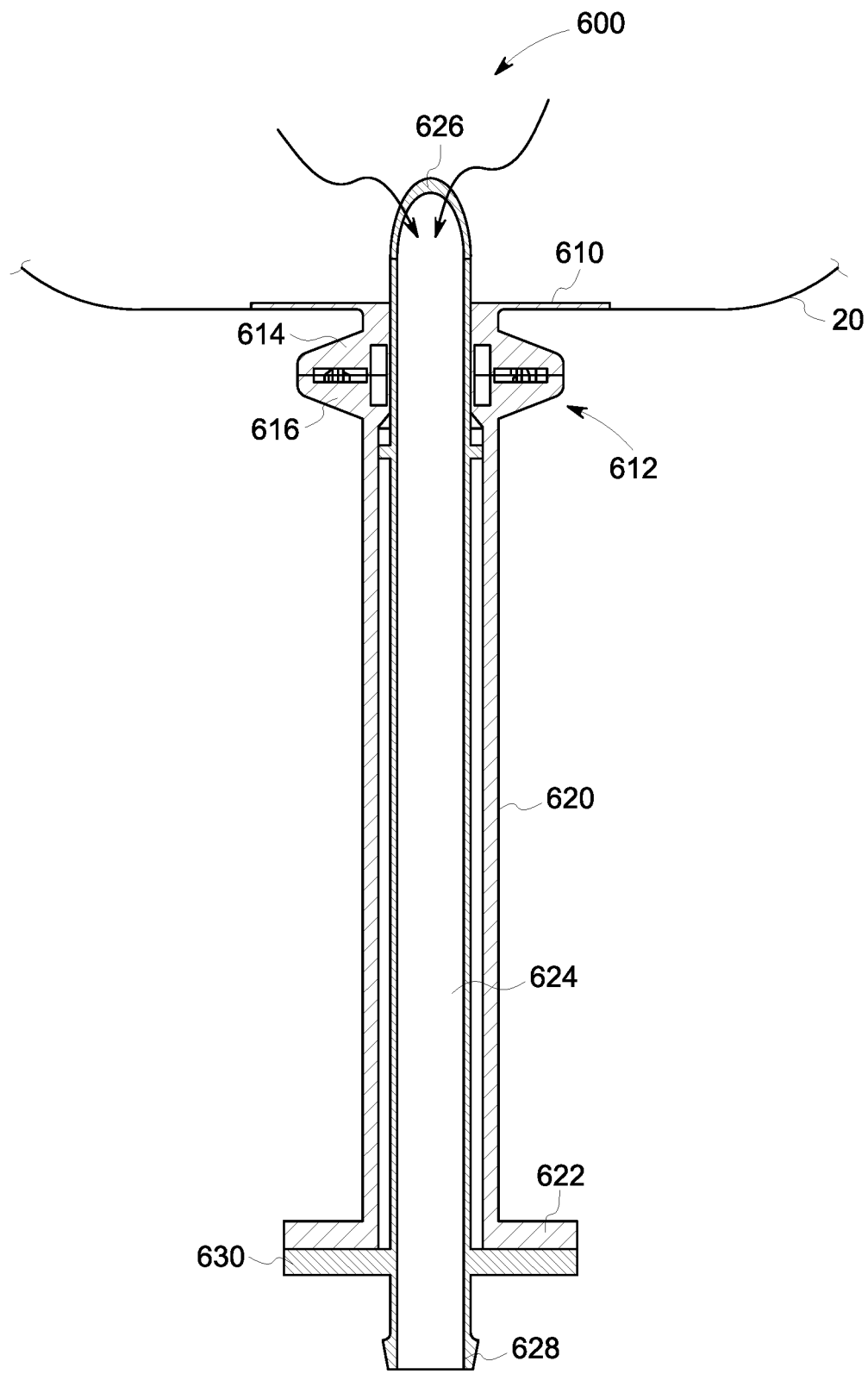
FIG. 19 is a side, cross-sectional view of the apparatus of FIG. 18, showing an open position whereby fluid flow is enabled.
Figure 20:
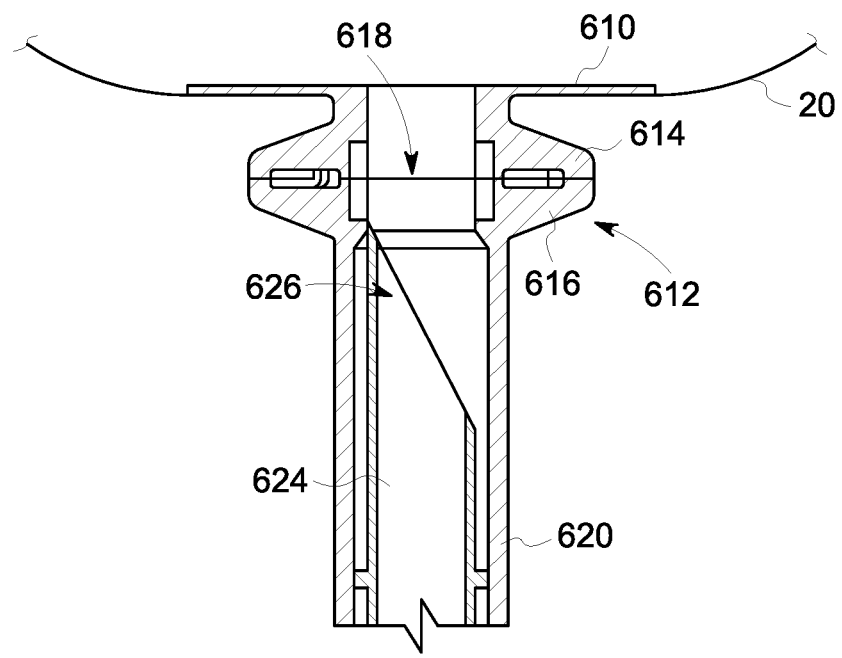
FIG. 20 is an enlarged, cross-sectional view of a piercing tip of the apparatus of FIG. 18.

Referring now to FIGS. 18-21, another apparatus 600 for preventing dead leg spaces in a bioprocessing system is illustrated. The apparatus 600 has a generally annular flange 610 configured for connection or integration with the flexible bag 20, and a connector 612 attached or integrally formed with the annular flange 610. In an embodiment, the connector 612 is an aseptic connector having a first connector member 614 and a second connector member 616 that matingly interface with one another and form a pierceable or fracturable seal or septum 618 therebetween. In an embodiment, the connector 612 is a ReadyMate™ disposable aseptic connector manufactured by General Electric®. As shown in FIGS. 18 and 19, the second connector member 616 is connected with, or integrally formed with, a hollow cylindrical tube or sleeve 620 that extends downwardly therefrom. A distal end of the sleeve 620 includes a flange forming a handle grip 622. While the connector 612 is illustrated as a two-piece component having a seal therebetween, in an embodiment, the connector may be a single component having a seal element that provides for fluid isolation between the interior of the flexible bag 20 and the sleeve 620.

Figure 21:
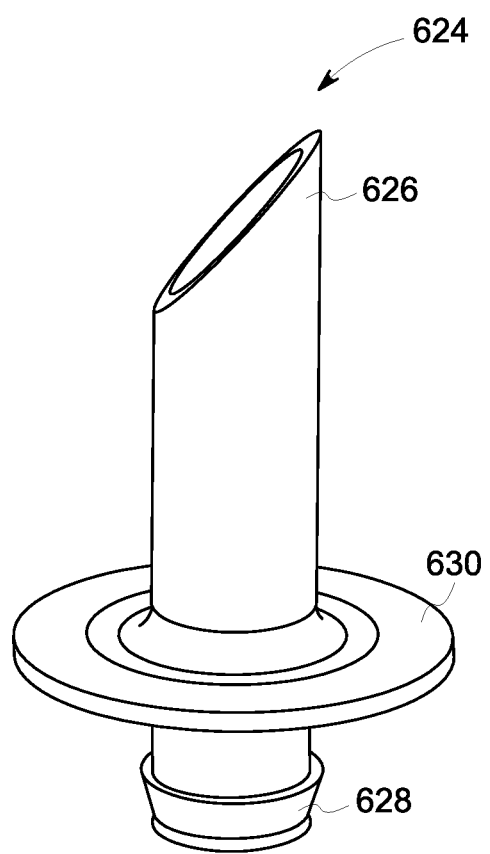
FIG. 21 is a perspective view of a spike member of the apparatus of FIG. 18.

As further shown in FIGS. 18 and 19, the apparatus 600 also includes a hollow spike 624 that is slidably received within the sleeve 620. As shown in FIG. 21, a terminal end of the spike 624 has a pointed, canoe-shaped tip 626 for piercing the seal 618, as discussed hereinafter. In an embodiment, the tip 626 may have any pointed shape suitable for piercing a thin membrane. An opposite, distal end of the spike 624 has a hose barb connection 628 for connection of drain tubing 26. In an embodiment, the spike 624 may also include a complementary flange forming a second handle grip 630.

With specific reference to FIG. 18, in use, the apparatus 600 is connected to a flexible bioprocessing bag 20 via the annular flange 610 in the manner described above. The hollow spike 624 is slidably received within the sleeve 620 such that the tip 626 is positioned below the seal element 618 of the connector 612. As illustrated in FIG. 18, in an embodiment, a removable clamp 632 may be positioned intermediate the flanges 622, 630 on the sleeve 620 and spike 624 to prevent accidental activation (i.e., accidental piercing of the seal element 618). In this state, the seal element 618 is positioned generally flush with the bottom of the flexible bag 20, so that the fluid within the bag 20 is not permitted to enter any cavities or tubing outside of the processing volume of the bag 20. Accordingly, dead leg spaces where settling can occur are substantially eliminated. Drain tubing 26 may be connected to the hose barb connection 628 on the distal end of the spike 624 either just before draining or at any time before draining after the bag 20 is positioned within the vessel 10. When it is desired to drain the bag 20 of its contents, the clamp 632 can be removed and the hollow spike 624 may be urged upwards into the bag. This movement of the spike 624 functions to pierce the seal element 618, causing the tip 626 of the spike 624 to enter the flexible bag 20, as shown in FIG. 19, providing a pathway for fluid to exit the flexible bag 20. In particular, fluid is able to flow into the hollow spike 624 and out the distal end thereof and into the connected drain tubing 26.

Figure 22:
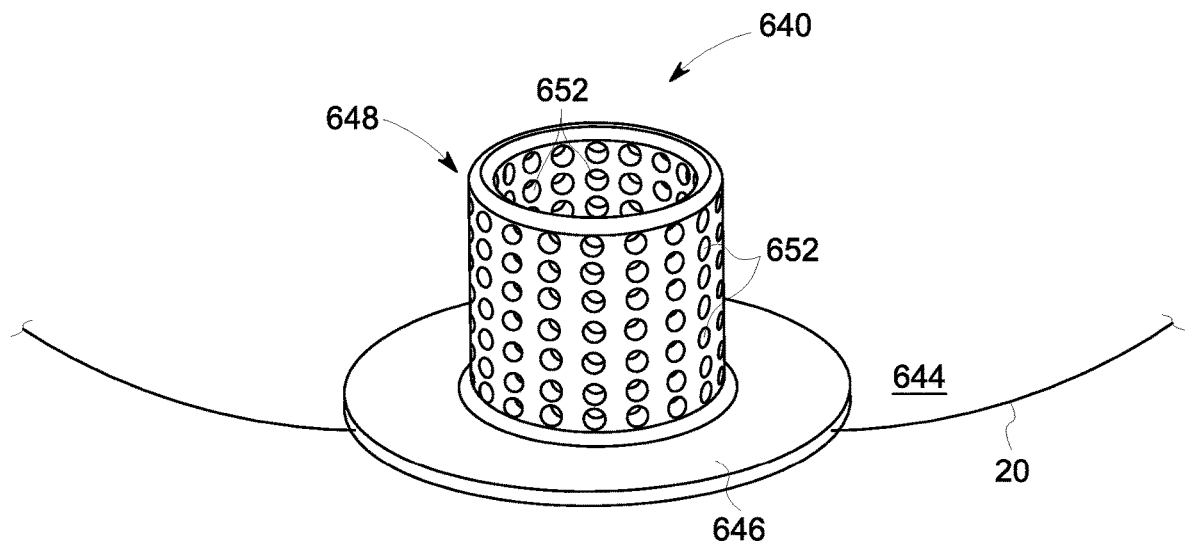
FIG. 22 is a perspective view of a protection element for use with the apparatus of FIG. 18, according to an embodiment of the invention.
Figure 23:
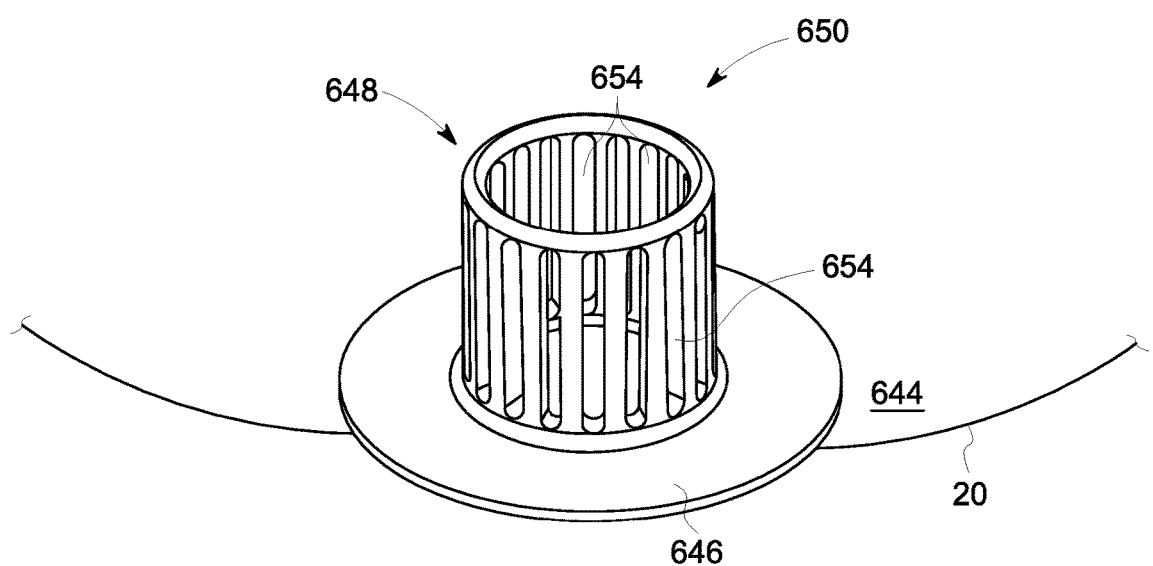
FIG. 23 is a perspective view of a protection element for use with the apparatus of FIG. 18, according to another embodiment of the invention.

In an embodiment, the apparatus 600 of FIGS. 18-21 may also employ a device that is configured to protect the integrity of the flexible bag 20 during a draining operation, including during piercing by the spike 624 and during the draining process. For example, as illustrated in FIGS. 22 and 23, a protection element 640, 650 maybe be positioned in the interior 644 to the flexible bag 20. The protection element 640, 650 may include a flange 646 configured for operative attachment or integration with the interior wall of the flexible bag 20, and an upstanding cage element 648 having a plurality of apertures 652 or slots 654 formed therein, as the case may be. In an embodiment, the flange 646 may be the same flange or a different flange than flange 610 of apparatus 600. The cage 648 functions to protect the flexible bag 20 from punctures when the spike is urged through the seal element during draining, and encloses the spike when it protrudes into the bag 20, preventing contact between the sharp tip of the spike and the bag 20. In an embodiment, different hole or slot patterns within the cage 648 may be employed to provide for optimal fluid flow. In an embodiment, the protection element 640, 650 may further include a cap (not shown) to prevent any cut portion of the bag 20 (which could result from the puncturing operation) from becoming loose inside the bag 20.

Figure 24:
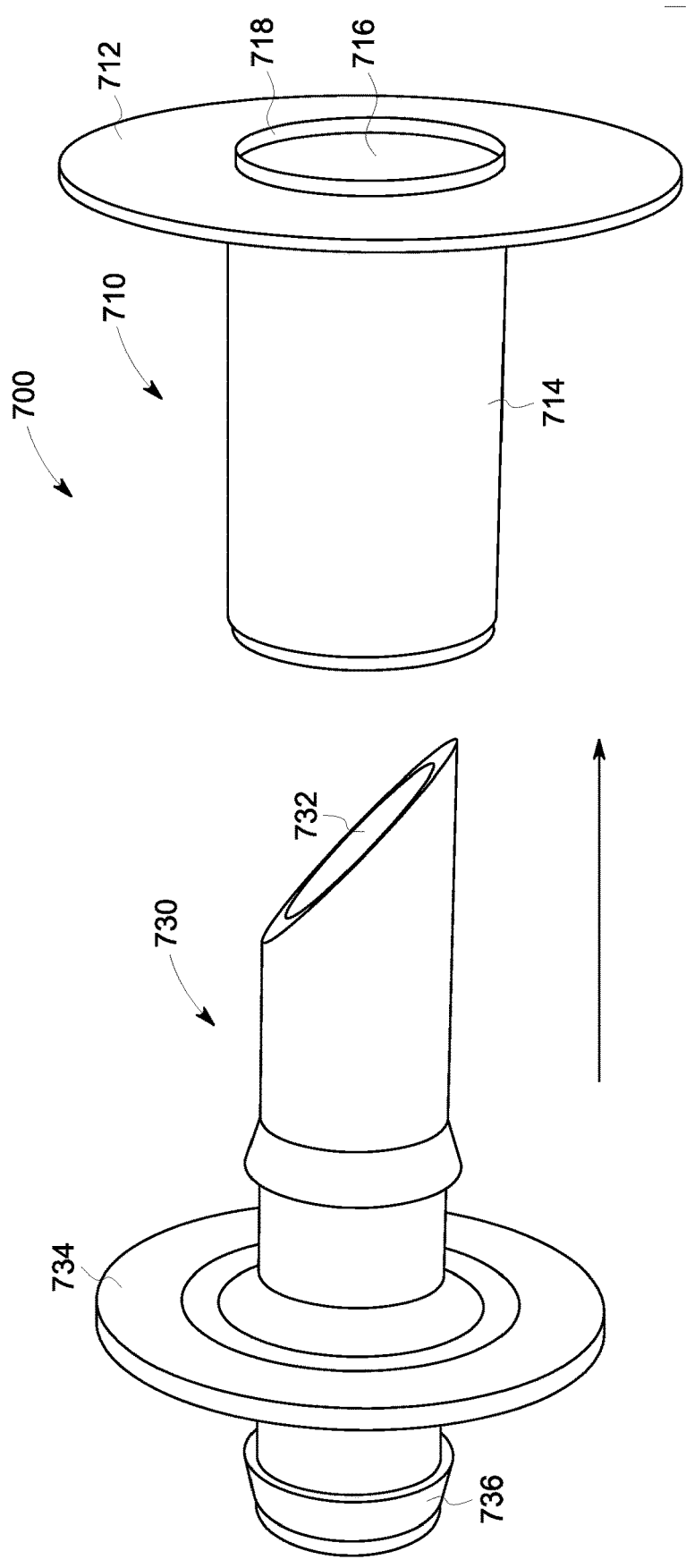
FIG. 24 is a perspective illustration of an apparatus for minimizing dead leg spaces in a bioprocessing system according to another embodiment of the invention.
Figure 25:
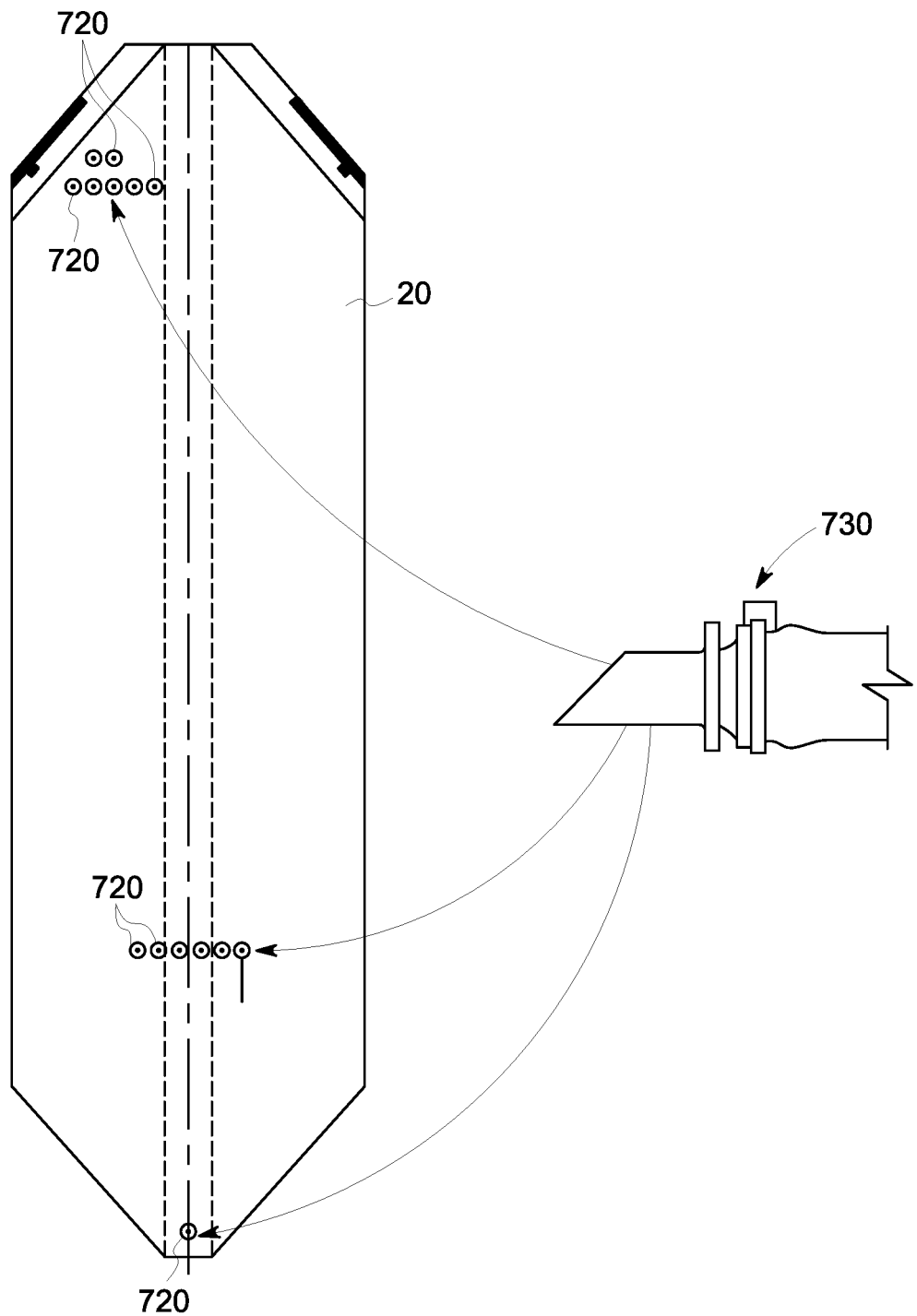
FIG. 25 is a schematic illustration of a flexible bag of a bioprocessing system, employing the apparatus of FIG. 24.

FIGS. 24 and 25 illustrate another apparatus 700 that is generally similar in configuration and operation to apparatus 600 described above, and functions to minimize dead leg spaces in a bioreactor or bioprocessing system. As illustrated therein, the apparatus 700 includes a port element 710 having a flange 712 and hollow cylindrical stem 714 depending therefrom. Like the embodiments described above, the flange 712 is configured for connection with the flexible bag 20 so that the stem 714 forms a passageway for fluid out of the bag 20. As shown in FIG. 24, the port element 710 includes a puncturable or fracturable membrane 716 and a flexible septum 718. While FIG. 24 depicts the membrane 716 as being located adjacent the flange 712, the membrane 716 may also be located within the stem 714 to minimize the possibility of accidental puncture. In an embodiment, and with reference to FIG. 25, port element 714 may be integrated with the flexible bag 20 at any location at which draining or sampling may be desired, thereby forming a plurality of accessible ports 720.

Referring once again to FIG. 24, apparatus 700 may also include a spike 730 for piercing the membrane 716 when accessing the contents of the bag 20 is desired, such as for draining or sampling. In an embodiment, the spike 730 may be substantially similar to spike 624 of FIGS. 18-21, and includes a pointed tip 732, flange 734 for gripping, and hose barb connection 736 for selectively connecting tubing for draining or other processes.

In operation, flexible bag 20 may be manufactured with a plurality of ports comprised of port elements 710. Accessing of the contents of the bag 20 is effectuated by inserting hollow spike 730 into the stem 714 to pierce the membrane 716. When the spike is urged into the bag 20, the septum 718 forms a seal around the outer periphery of the spike 730, preventing leaking. In this position, fluid is permitted to flow into the spike 730 and out of the connected tubing. In yet other embodiments, the septum functions as a self-sealing element, whereby the spike 730 may be thrust into the bag 20 for draining or sampling, and when the spike 730 is retracted or removed, the septum functions to close the opening and prevent fluid leakage.

Figure 26:
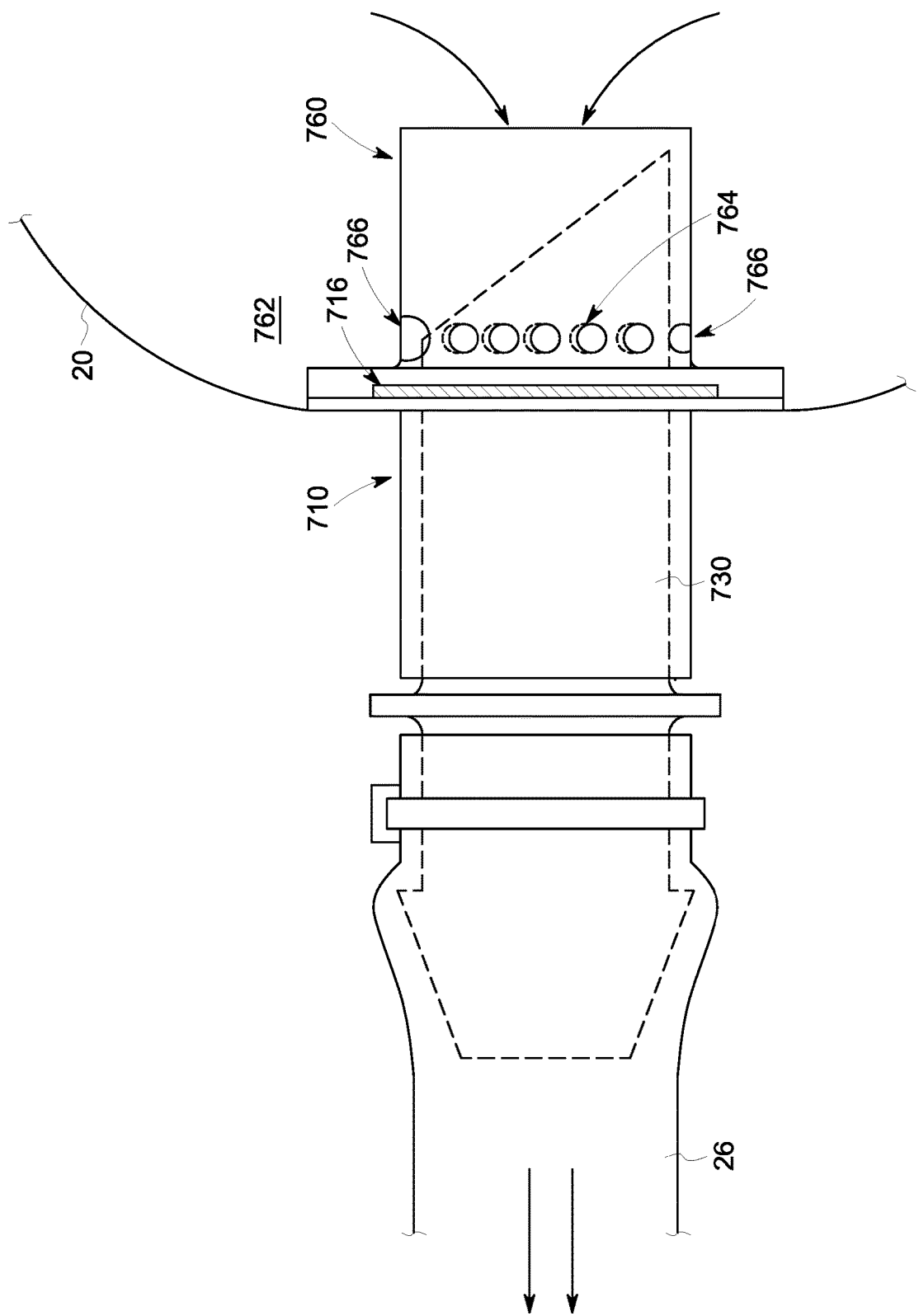
FIG. 26 is a schematic illustration of an apparatus for minimizing dead leg spaces in a bioprocessing system, according to another embodiment of the invention.
Figure 27:
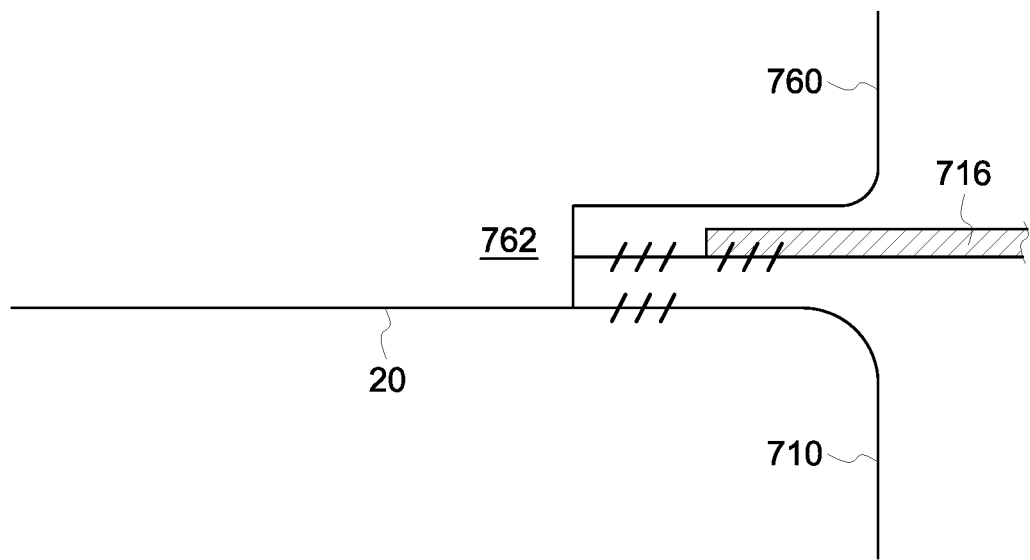
FIG. 27 is an enlarged, detail view of a sealing interface of the apparatus of FIG. 26.

Turning now to FIG. 26, in an embodiment, the port element 710 may be utilized in conjunction with a protection element 760 that is positioned interior 762 to the flexible bag 20. In an embodiment, the protection element 760 may take the form of protection element 640 or 650 shown in FIGS. 22 and 23 and described above. As described hereinbefore, the protection element 760 functions to prevent inadvertent puncture or tearing of the flexible bag when the spike 730 is urged into the bag 20 during draining. As shown in FIG. 26, in embodiments where the apparatus includes a protection element 760, the membrane 716 may be sandwiched between the flange of the port element and the flange of the protection element. This configuration is more clearly shown in FIG. 27. As shown in FIGS. 26 and 27, in an embodiment, the spike 730 itself may include a plurality of apertures 764 for the passage of fluid. In particular, the spike 730 may have a plurality of apertures 764 that are placed in close association with the apertures 766 in the protection element 760 when the spike 730 is thrush into the flexible bag 20. This configuration facilitates fluid flow at low volumes in the bag.

Figure 28:
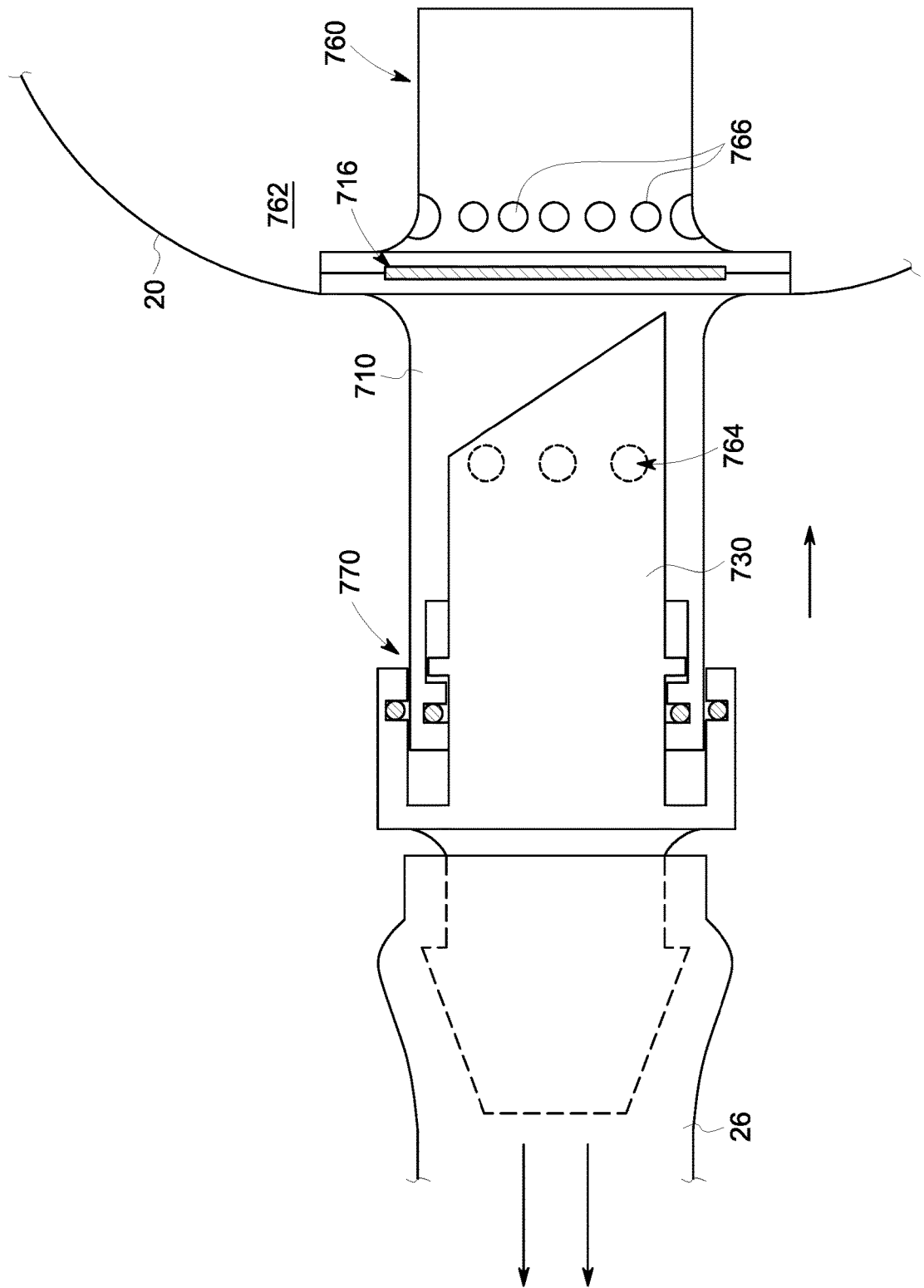
FIG. 28 is a schematic illustration of an apparatus for minimizing dead leg spaces in a bioprocessing system, according to another embodiment of the invention.

With reference to FIG. 28, in an embodiment, the spike 730 may be integrated into the port element 710 as a sterile connector. As shown the spike 730 and port connector are substantially similar to those in apparatus 700 described above, however, the apparatus further includes a sterile connection mechanism 770. In any of the embodiments described above in connection with FIGS. 24-28, it is contemplated that the spike 730 may be coupled to an actuator to facilitate automatic piercing of the membrane and entry into the bag.

Figure 29:
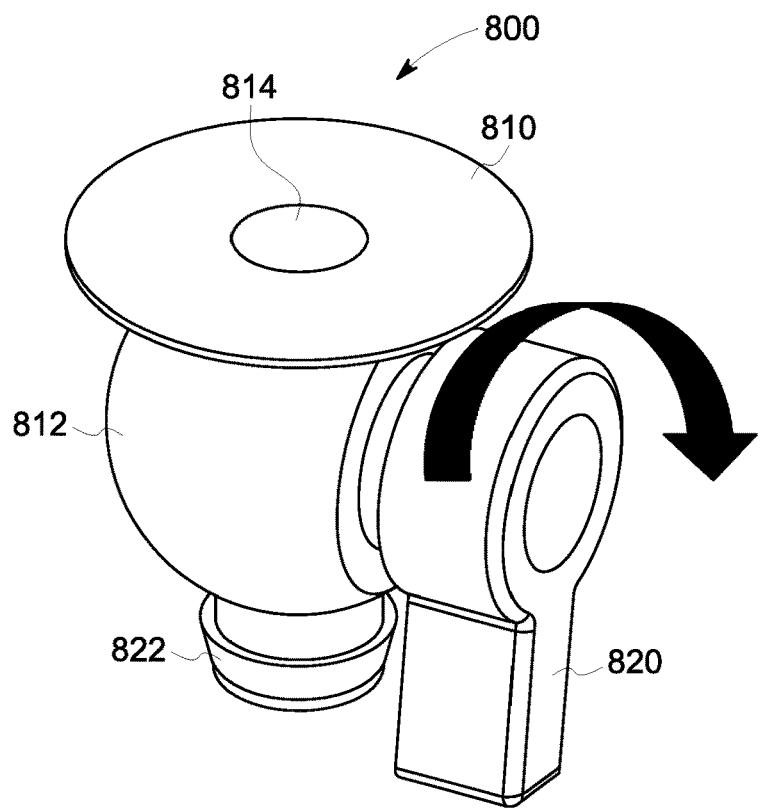
FIG. 29 is a perspective view of an apparatus for minimizing dead leg spaces in a bioprocessing system according to another embodiment of the invention.
Figure 30:
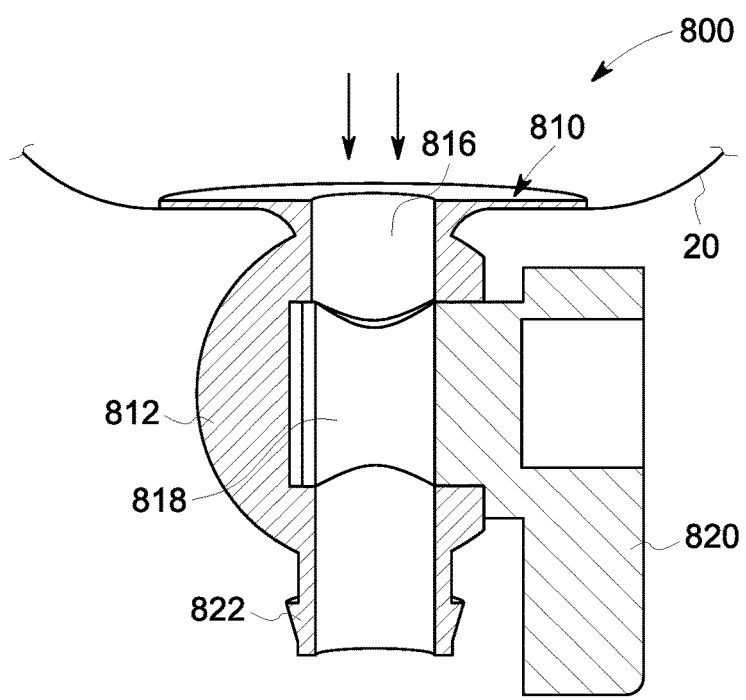
FIG. 30 is a cross-sectional view of the apparatus of FIG. 29.
Figure 31:
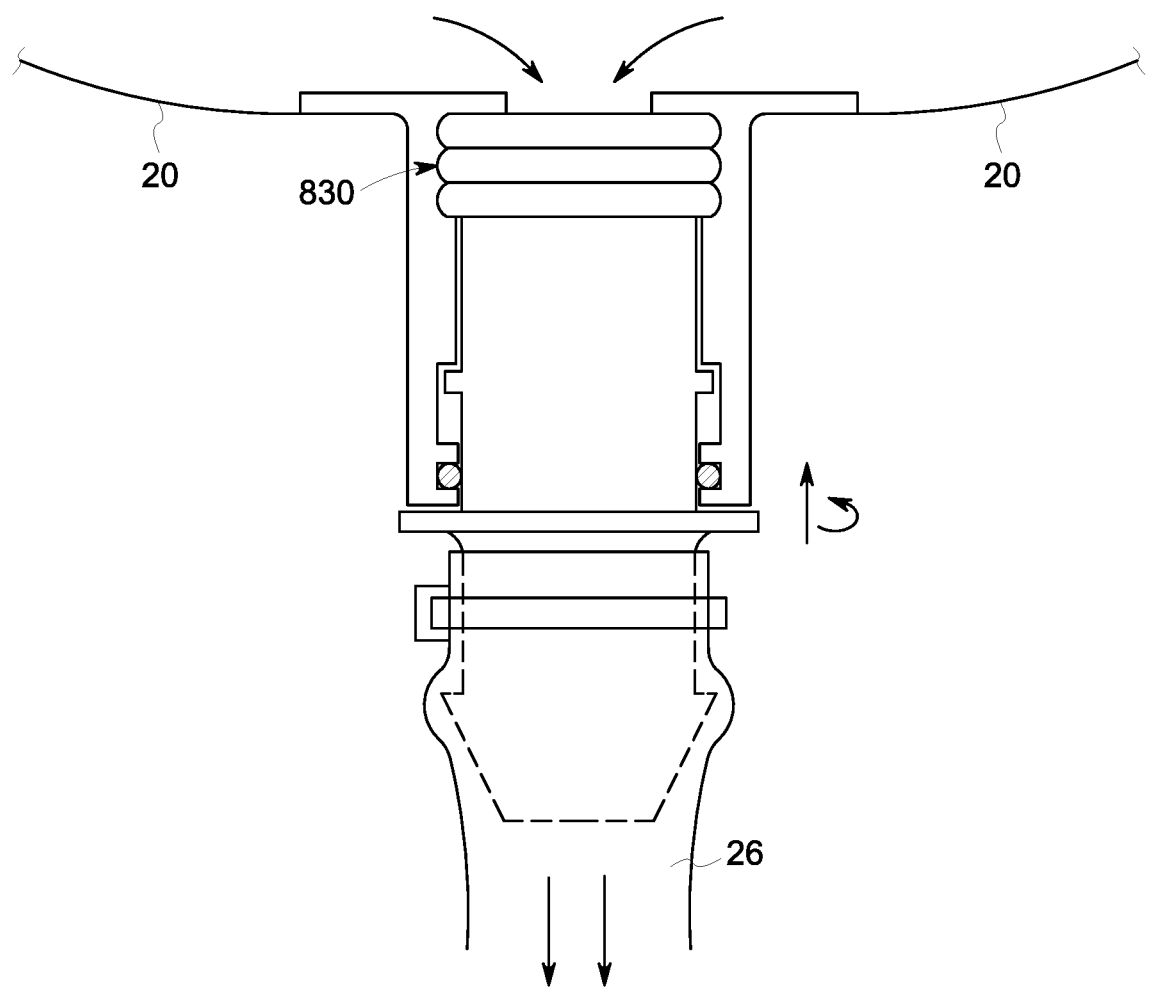
FIG. 31 is a schematic illustration of an apparatus for minimizing dead leg spaces, employing a septum, according to an embodiment of the invention.

Turning finally to FIGS. 29-31, yet another apparatus 800 for minimizing or preventing dead leg spaces in a bioprocessing system is illustrated. The apparatus 800 includes a flange 810 and a generally spherical main body 812 operatively connected thereto. The flange 810 includes an opening 814 in fluid communication with a fluid flow passageway 816 that extends through the main body portion 812. The main body portion also includes a valve 818 positioned within the fluid flow passageway 816, and an actuator handle or lever 820 that is rotatable to selectively open or close the valve 818. In an embodiment, the valve 818 and lever 820 form a stopcock. As shown in FIGS. 29 and 30, a lower end of the main body 812 may include a hose barb connection 822 for connecting drain tubing 26 in the manner described above.

In use, the apparatus 800 may be operatively connected to the flexible bag 20 via the flange 810 in the manner described above. A user may then rotate the lever 820 to selectively open or close the valve 818 to allow or prevent fluid flow out of the bag 20. It is contemplated that the apparatus 800 may be used throughout a bioprocess where a drain valve may be opened and closed multiple times. In addition, the openable and closeable nature of the apparatus 800 facilitates the use of the apparatus 800 for both draining and feeding operations. In an embodiment, it is contemplated that the lever 820 may be coupled to an actuator to facilitate automatic operation of the valve 818.

It is contemplated that a septum may be incorporated into the design of any of the apparatuses described herein, such as apparatus 800, to further minimize any potential dead leg volume. FIG. 31 illustrates the position of a septum 830 that can be integrated with one or more of the embodiments described herein.

Figure 32:
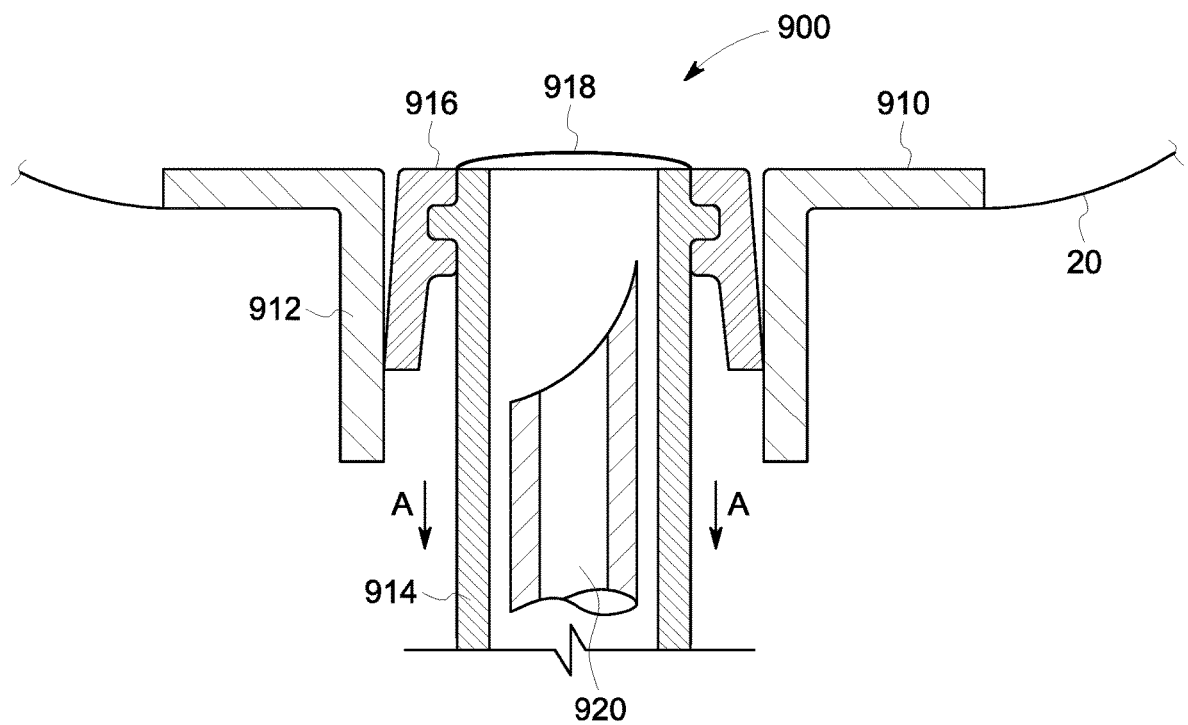
FIG. 32 is a side, cross-sectional view of an apparatus for minimizing dead leg spaces in a bioprocessing system according to another embodiment of the invention, showing a closed position.
Figure 33:
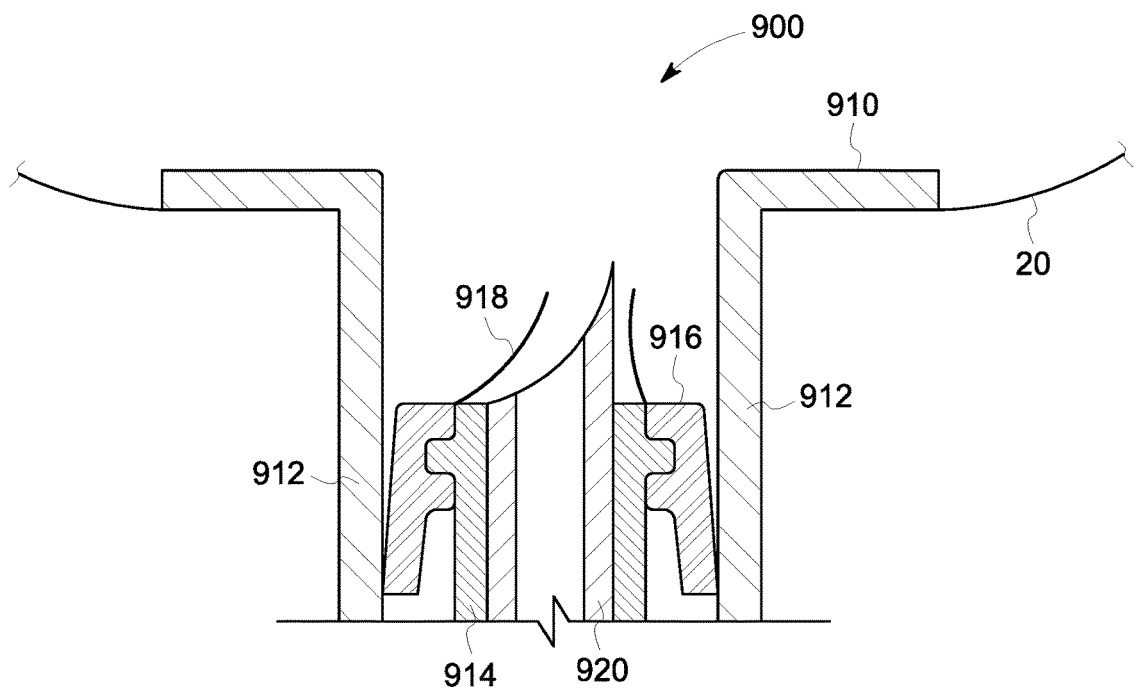
FIG. 33 is a side, cross-sectional view of the apparatus of FIG. 32, showing an open position.

Referring now to FIGS. 32 and 33, another apparatus 900 for preventing dead leg spaces in a bioprocessing system is illustrated. The apparatus 900 has a generally annular flange 910 configured for connection or integration with the flexible bag 20, such as through welding, as discussed above. The annular flange 910 includes a depending leg portion defining a generally cylindrical, hollow outer sleeve 912. Within the outer sleeve 912 is slidably received a hollow inner sleeve 914. The inner sleeve 914 may include a gasket 916 that is configured to sealingly engage the inner wall of the outer sleeve 912 to prevent a flow of fluid therethrough. As illustrated in FIG. 32, the inner sleeve 914 also includes a thin membrane 918 that extends across a top opening of the inner sleeve 914 to prevent a flow of fluid from the bag 20 into the inner sleeve 914. The apparatus 900 further includes a hollow spike 920 or piercing member in static position within the inner sleeve 914 below the membrane 918.

In operation, to drain the bag 20, a lower portion of the inner sleeve 914 is gripped and pulled downwardly, in the direction of arrow A. This movement causes the gasket 916 to slide along the inner surface of the outer sleeve 912. Continued downward urging of the inner sleeve 914 brings the membrane 918 into contact with the sharp tip of the spike 920, causing the spike to pierce through the membrane 918, as shown in FIG. 33. In this position, the fluid within the bag is permitted to flow past the tear in the membrane 918 and through the spike 920 to drain the contents of the bag 20.

Figure 34:
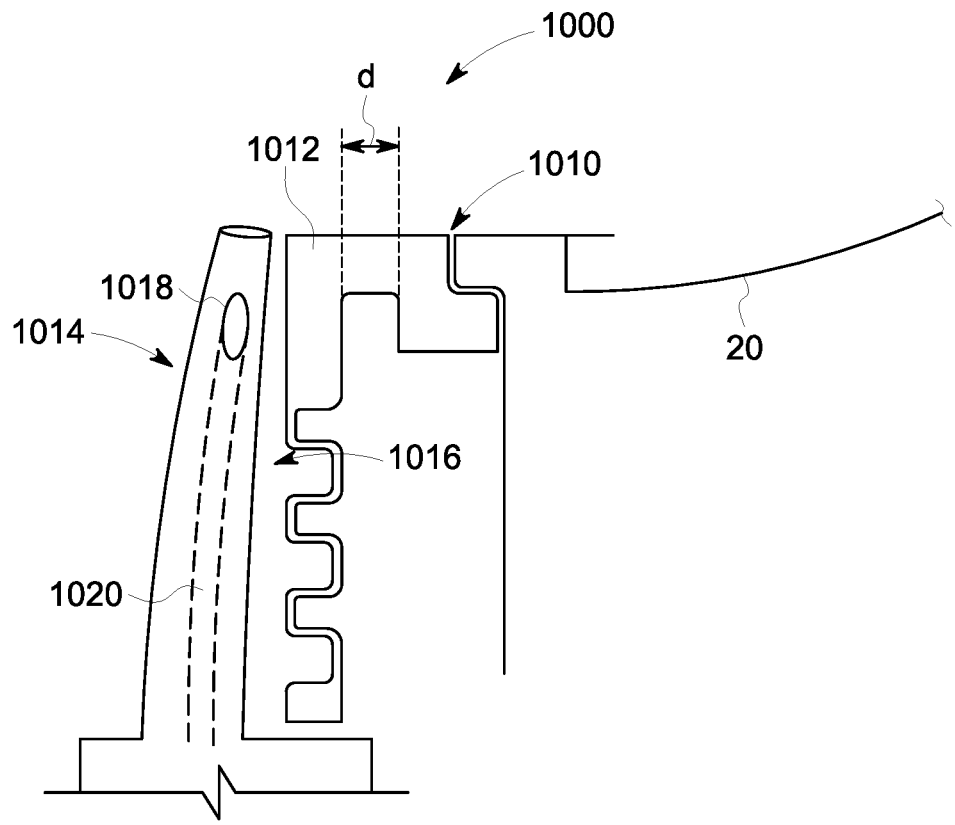
FIG. 34 is a side, cross-sectional view of an apparatus for minimizing dead leg spaces in a bioprocessing system, according to another embodiment of the invention, showing a closed position.
Figure 35:
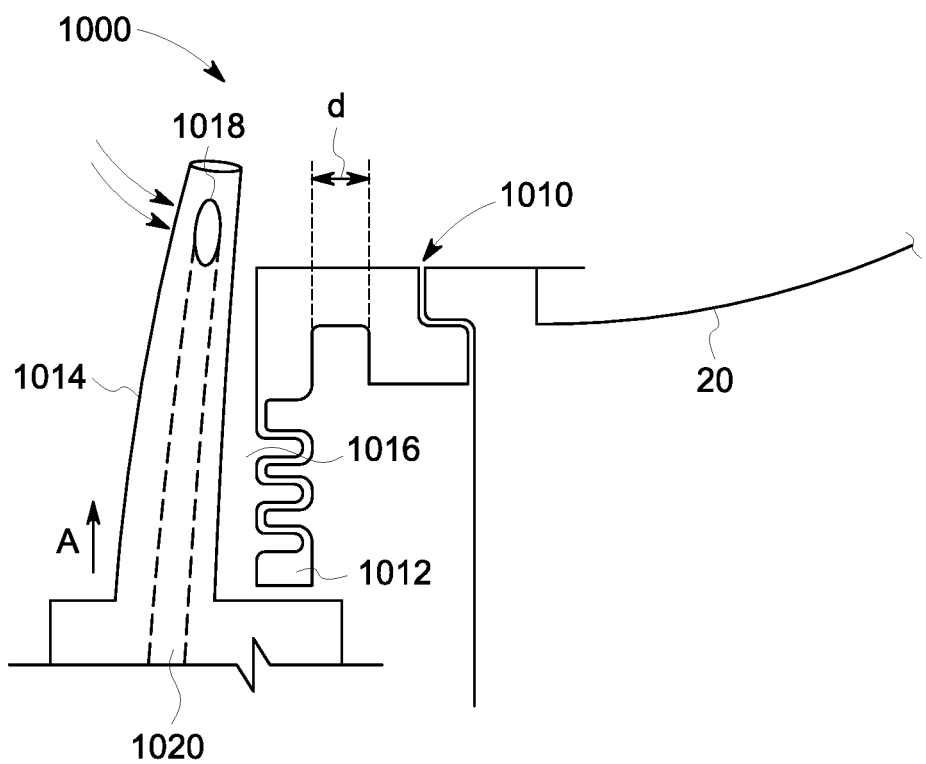
FIG. 35 is a side, cross-sectional view of the apparatus of FIG. 34, showing an open position.

Referring to FIGS. 34 and 35, another apparatus 1000 for preventing dead leg spaces in a bioprocessing system is illustrated. The apparatus 1000 is configured to positioned within a drain port 1010 of a flexible processing bag 20. In an embodiment, the drain port may be configured with an annular flange that is welded to the bag 20 and has a cylindrical outlet opening for draining the contents of the bag, similar to those described above. The apparatus 1000 includes a compressible gasket 1012 (one half of which is shown in FIGS. 34 and 35) positioned within the drain port 1010, and a clave device/needle 1014 received within a central passageway 1016 of the gasket 1012. As shown therein, the clave needle 1014 includes a fluid opening 1018 at the top thereof, and a central fluid passageway 1020 extending from the opening 1018 through the needle 1014.

As shown in FIG. 34, in a closed position, the opening 1018 is positioned below the bottom surface of the bag 20 (and or a top surface of the gasket 1012) so that fluid cannot flow into the opening 1018. With reference to FIG. 35, to drain the bag 20, the clave needle 1014 is urged upwardly in the direction of arrow A until the opening 1018 is in fluid communication with interior of the bag 20, enabling the contents to be drained through the opening 1018 and fluid passageway 1020. As shown therein, upward movement of the clave needle 1014 compresses the gasket 1012, decreasing the distance, d, of a lateral portion of the gasket, due to the tapered configuration of the external surface of the clave needle 1014.

Figure 36:
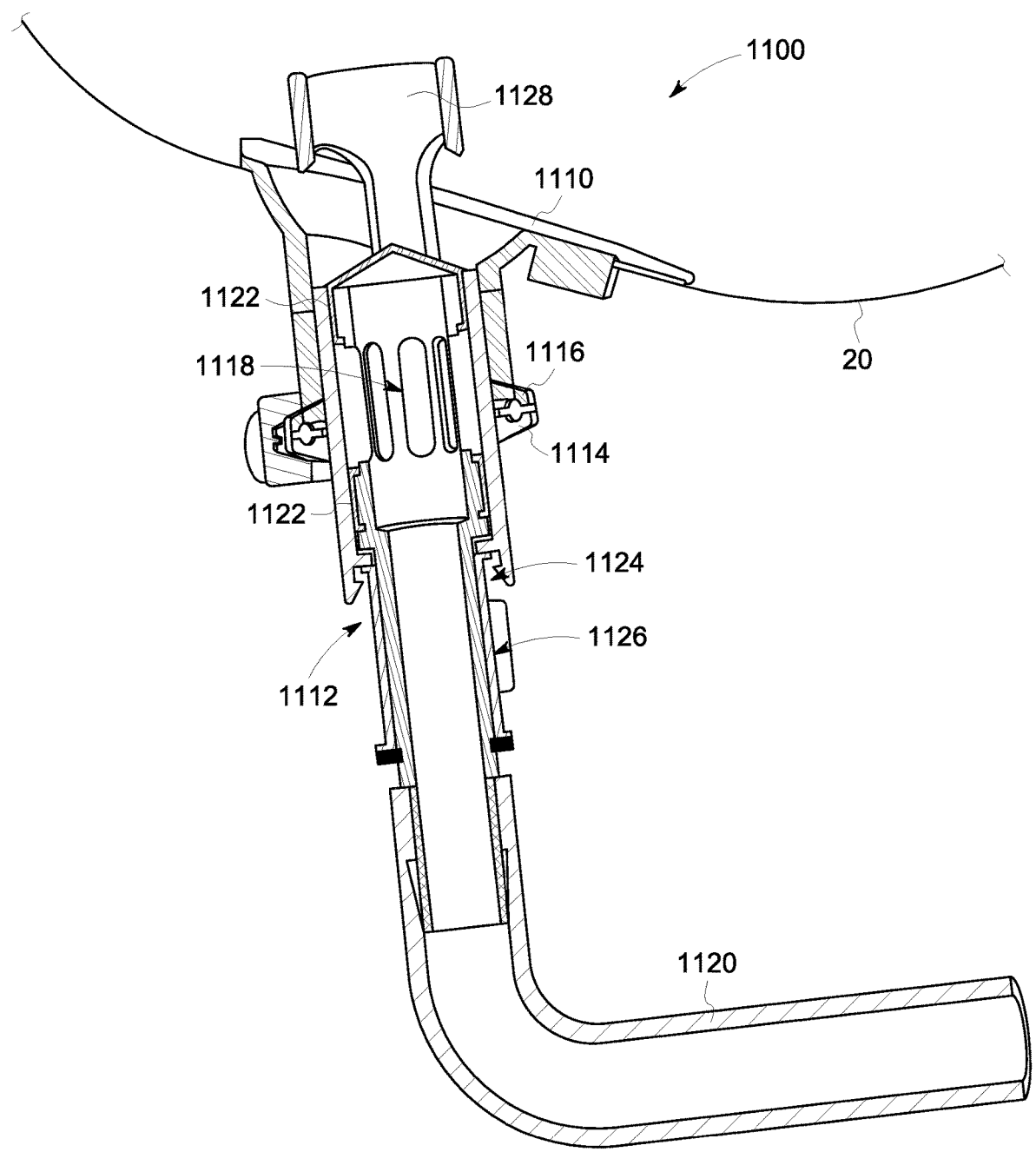
FIG. 36 is a cross-sectional, perspective view of an apparatus for minimizing dead leg spaces in a bioprocessing system, according to another embodiment of the invention.

Referring finally to FIG. 36, another apparatus 1100 for preventing dead leg spaces in a bioprocessing system is illustrated. The apparatus 1100 is configured to positioned within a drain port 1110 of a flexible processing bag 20. In an embodiment, the drain port 1110 may be configured with an annular flange that is welded to the bag 20 and has a cylindrical outlet opening for draining the contents of the bag, similar to those described above. The apparatus 1100 is generally similar to the embodiment shown in FIGS. 18 and 19 and includes a syringe assembly 1112 which is connected to the bag port 1110 via first and second mating connectors 1114, 1116. The syringe assembly 1112 includes a hollow plunger 1118, a lower end of which is configured for connection to drain tubing 1120. Similar to the embodiments described above, the plunger 1118 is slidably upwardly into the bag 20 to allow fluid communication with the openings in the plunger 1118 and the interior of the bag 20. As shown in FIG. 36, seal elements 1122 may form a fluid seal with the interior of the port 1110. The apparatus 1100 may also include a locking mechanism 1124 (e.g., a latch or L-lock mechanism) and a safety device 1126 that prevents upward travel of the plunger 1118 until the safety device 1126 is removed. The apparatus 1100 may further include a cage element 1128 to protect the bag 20 from puncture when the plunger 1118 is urged upwardly into the interior of the bag.

As described herein, embodiments of the invention described can be utilized to prevent or substantially minimize dead leg spaces in a bioprocessing system and, particularly, in the drain tubing an associated connectors or components of the drain system of a bioreactor. By minimizing dead leg spaces, media, cells and other fluid components are prevented from settling in areas where they can be isolated from the main bioreactor environment, which minimizes the likelihood that the cells will be deprived of nutrients and die. Accordingly, by minimizing these dead leg spaces, maximum yield may be achieved and sedimentation is reduced.

In an embodiment, an apparatus for minimizing dead leg spaces in a container or tubing includes a first member having a flange for attaching the first member to a wall of the container or tubing, the flange having at least one aperture, and a second member rotatably coupled to the first member, the second member having an upper end having at least one aperture, and an open distal end. The second member is rotatable relative to the first member between a closed position where the at least one aperture of the second member is misaligned with the at least one aperture in the flange to prevent the passage of fluid, and an open position where the at least one aperture of the second member is aligned with the at least one aperture in the flange to allow for the passage of fluid. In an embodiment, the at least one aperture in the flange is a plurality of apertures radially offset from a centerline of the flange, and the at least one aperture in the upper end of the second member is a plurality of apertures corresponding to the plurality of aperture of the flange. The plurality of apertures in the upper end of the second member are at radial and angular locations that correspond to radial and angular locations of the plurality of apertures of the flange. In an embodiment the first member may include one of a keyway and a projection and the second member may include the other of the keyway and the projection, wherein the keyway and the projection are operable to selectively lock the second member in the open position. In an embodiment the first member includes a pair of resilient arms and the second member includes a circumferential groove, wherein the resilient arms engage the circumferential groove and facilitate rotation of the second member between the open position and the closed position. In an embodiment, the circumferential groove includes at least one position stop, the at least one position stop limiting rotation of the second member with respect to the first member. In an embodiment the at least one position stop is located such that rotation of second member to a position where one of the resilient arms contacts the position stop corresponds to the open position of the apparatus. In an embodiment the first member includes a first threaded portion and the second member includes a second threaded portion configured to threadedly engage the first threaded portion to allow rotation of the second threaded portion with respect to the first threaded portion. In an embodiment the distal end of the second member includes a hose barb connector for connecting drain tubing to the apparatus. In an embodiment the container or tubing is a flexible, single-use bioprocessing bag.

In another embodiment, an apparatus for minimizing dead leg spaces in a container or tubing includes a first member having a flange for attaching the first member to a wall of the container or tubing, and a generally hollow sleeve extending from the flange, and a plunger slidably received within the hollow sleeve, the plunger having a tip configured to sealingly engage the first member. The plunger is slidable between a closed position where the tip sealingly engages the sleeve adjacent to the flange to prevent the passage of fluid into the sleeve, and an open position where the plunger is linearly displaced from the closed position to allow for the passage of fluid into the sleeve. In an embodiment, the plunger includes at least one relieved area or passageway below the tip allowing for the passage of fluid. In an embodiment, the first member further includes a branch leg extending from the sleeve, the branch leg terminating in a hose barb connector for connection of drain tubing. In an embodiment, the plunger includes one of an L-shaped keyway and a lug and the sleeve includes the other of the keyway and the lug, and the plunger is rotatable and moveable linearly with respect to the sleeve such that when the lug is received in an upper portion of the keyway the plunger is in the closed position, and when the lug is received in a lower portion of the keyway the plunger is locked in the open position. In an embodiment, the plunger includes a handle on a distal end of the plunger. In an embodiment, the container or tubing is a flexible, single-use bioprocessing bag.

In yet another embodiment, an apparatus for minimizing dead leg spaces in a container or tubing includes a first member having a flange for attaching the first member to a wall of the container or tubing, a generally hollow sleeve extending from the flange, and a sealing element extending across the sleeve for sealing off a passage through the sleeve, and a generally hollow piercing member slidably received within the hollow sleeve, the piercing member having a piercing tip. The piercing member is movable between a first position where the piercing tip is positioned below the sealing element whereby the sealing element remains intact to prevent the passage of fluid beyond the sealing element, and a second position where the piercing member pierces the sealing element and the piercing tip extends into the container or tubing and an interior of the piercing member is in fluid communication with an interior of the container or tubing to allow for passage of fluid into the hollow piercing member and beyond the sealing element. In an embodiment, the sealing element forms a part of an aseptic connector integrated with the first member. In an embodiment, the apparatus further includes a protection element positioned interior to the container or tubing the protection element having a sidewall that surrounds an opening in the flange to prevent contact of the piercing tip with the container or tubing, and the sidewall includes a plurality of slots or apertures for the passage of fluid. In an embodiment, the piercing member includes a hose barb connector on a distal end of the piercing member for connecting drain tubing to the apparatus.

In yet another embodiment, an apparatus for minimizing dead leg spaces in a container or tubing includes a flange for attaching the first member to a wall of the container or tubing, the flange including an opening, a main body connected to the flange, the main body having a passageway in fluid communication with the opening in the flange, a connection member connected to the main body for connecting drain tubing to the apparatus, and a valve positioned within the passageway, the valve being actuatable between a closed position in which fluid flow through the passageway is prevented, and an open position in which fluid flow through the passageway is allowed.

In yet further embodiments, a bioprocessing system is provided. The system includes a single-use, flexible bioreactor bag having drain opening or outlet port, and an apparatus or device positioned within the drain opening and attached to the flexible bag, for minimizing dead leg spaces in the flexible bioreactor bag and/or associated drain tubing and/or components. The apparatus may be any one of the apparatuses described above in connection with FIGS. 2-31.

In yet other embodiments, a method for minimizing dead leg spaces in a container or tubing of a bioprocessing is provided. The method includes positioning a flexible, single-use bioreactor bag within a support vessel, the flexible bioprocessing bag including a device configured to minimize dead leg spaces positioned in an outlet port or drain opening in the flexible bag, and connecting a drain tube to the device. The device may be any one of the apparatuses described above in connection with FIGS. 2-31. The method also includes actuating the device to place the interior of the flexible bag in fluid communication with the drain tube so that fluid from the flexible bag may flow through the device and into the drain tube.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for minimizing dead leg spaces in a container or tubing, comprising:
    a first member having a flange for attaching the first member to a wall of the container or tubing and a hollow stem extending downwardly from the flange and having a central axis that is perpendicular to the flange, the flange having a top, upwardly-facing surface and at least one aperture in the top surface; and
    a second member having a tubular body portion having a top, upwardly-facing surface and at least one aperture in the top surface, and an open distal end, the second member being rotatably coupled to the first member;
    wherein the second member is rotatable relative to the first member between a closed position where the at least one aperture of the second member is misaligned with the at least one aperture in the flange to prevent the passage of fluid, and an open position where the at least one aperture of the second member is aligned with the at least one aperture in the flange to allow for the passage of fluid;
    wherein the second member is axially fixed with respect to the first member such that during rotation of the second member relative to the first member, an axial position of the second member with respect to the first member is maintained.

2. The apparatus of claim 1, wherein:
    the first member includes a pair of resilient arms each having a distal end that projects inwardly toward the central axis; and
    the second member includes a circumferential groove that extends substantially entirely around the second member;
    wherein the resilient arms engage the circumferential groove and facilitate rotation of the second member between the open position and the closed position.

3. The apparatus of claim 2, wherein:
    the circumferential groove includes at least one position stop, the at least one position stop limiting rotation of the second member with respect to the first member.

4. The apparatus of claim 3, wherein:
    the at least one position stop is located such that rotation of second member to a position where one of the resilient arms contacts the position stop corresponds to the open position of the apparatus.

5. The apparatus of claim 1 wherein:
    the distal end of the second member includes a hose barb connector for connecting drain tubing to the apparatus.

6. The apparatus of claim 1, wherein:
    the container or tubing is a flexible, single-use bioprocessing bag.

7. The apparatus of claim 1, wherein:
    the top surface of the tubular body portion of the second member is generally coplanar with the top surface of the flange in both the closed position and the open position.

8. The apparatus of claim 1, wherein:
    the hollow stem of the first member and the tubular body portion of the second member define therethrough a hollow passageway defining an axial direction; and
    wherein in the open position, the aperture in the flange of the first member and the aperture in the top surface of the tubular body portion of the second member are aligned in the axial direction.

* * * * *